US010732183B2

(12) United States Patent
Ju et al.

(10) Patent No.: US 10,732,183 B2
(45) Date of Patent: Aug. 4, 2020

(54) METHOD FOR DETECTING MULTIPLE PREDETERMINED COMPOUNDS IN A SAMPLE

(71) Applicants: Jingyue Ju, Englewood Cliffs, NJ (US); Shiv Kumar, Belle Mead, NJ (US); Chuanjuan Tao, New York, NY (US); Sergey Kalachikov, New York, NY (US); James J. Russo, New York, NY (US)

(72) Inventors: Jingyue Ju, Englewood Cliffs, NJ (US); Shiv Kumar, Belle Mead, NJ (US); Chuanjuan Tao, New York, NY (US); Sergey Kalachikov, New York, NY (US); James J. Russo, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 338 days.

(21) Appl. No.: 14/776,461

(22) PCT Filed: Mar. 14, 2014

(86) PCT No.: PCT/US2014/029495
§ 371 (c)(1),
(2) Date: Sep. 14, 2015

(87) PCT Pub. No.: WO2014/144898
PCT Pub. Date: Sep. 18, 2014

(65) Prior Publication Data
US 2016/0041179 A1 Feb. 11, 2016

Related U.S. Application Data

(60) Provisional application No. 61/799,276, filed on Mar. 15, 2013.

(51) Int. Cl.
| | |
|---|---|
| *C12Q 1/68* | (2018.01) |
| *C07H 21/00* | (2006.01) |
| *G01N 33/68* | (2006.01) |
| *G01N 33/487* | (2006.01) |
| *C08G 65/48* | (2006.01) |

(52) U.S. Cl.
CPC ......... *G01N 33/6818* (2013.01); *C08G 65/48* (2013.01); *G01N 33/48721* (2013.01)

(58) Field of Classification Search
CPC .................. C12Q 1/68; C07H 21/00
See application file for complete search history.

(56) References Cited

U.S. PATENT DOCUMENTS

| | | | |
|---|---|---|---|
| 5,756,355 A | 5/1998 | Lang et al. |
| 5,770,367 A | 6/1998 | Southern et al. |
| 5,795,782 A | 8/1998 | Church et al. |
| 5,804,386 A | 9/1998 | Ju et al. |
| 5,814,454 A | 9/1998 | Ju |
| 5,876,936 A | 3/1999 | Ju |
| 5,952,180 A | 9/1999 | Ju et al. |
| 6,015,714 A | 1/2000 | Baldarelli et al. |
| 6,046,005 A | 4/2000 | Ju et al. |
| 6,362,002 B1 | 3/2002 | Denison et al. |
| 6,383,749 B2 | 5/2002 | Bochkariov et al. |
| 6,399,335 B1 | 6/2002 | Kao et al. |
| 6,413,792 B1 | 7/2002 | Sauer et al. |
| 6,485,703 B1 | 11/2002 | Cotè et al. |
| 6,616,895 B2 | 9/2003 | Dugas et al. |
| 6,627,748 B1 | 9/2003 | Ju et al. |
| 6,664,079 B2 | 12/2003 | Ju et al. |
| 6,673,615 B2 | 1/2004 | Denison et al. |
| 6,746,594 B2 | 6/2004 | Akeson et al. |
| 6,916,665 B2 | 7/2005 | Bayley et al. |
| 7,074,597 B2 | 7/2006 | Ju |
| 7,189,503 B2 | 3/2007 | Akeson et al. |
| 7,238,485 B2 | 7/2007 | Akeson et al. |
| 7,279,337 B2 | 10/2007 | Zhu |
| 7,345,159 B2 | 3/2008 | Ju et al. |
| 7,622,279 B2 | 11/2009 | Ju |
| 7,622,934 B2 | 11/2009 | Hibbs et al. |
| 7,625,701 B2 | 12/2009 | Williams et al. |
| 7,635,578 B2 | 12/2009 | Ju et al. |

(Continued)

FOREIGN PATENT DOCUMENTS

| | | |
|---|---|---|
| WO | WO2001094609 | 12/2001 |
| WO | WO 02/22883 | 3/2002 |

(Continued)

OTHER PUBLICATIONS

Chu et al., Nucleic Acids Research 16(9) : 3671 (1988).*
Hornblower et al., Nature Methods 4(4) : 315 (2007).*
Meller et al., Physical Review Letters 86 (15) : 3435 (2001).*
Scheider et al., Nano Letters 10: 3163 (2010).*
Winters-Hilt et al., BMC Bioinformatics 7 (Suppl 2); 521 (2006).*
Winters-Hilt, S., BMC Bioinformatics 8 (Suppl 7); S9 (2007).*
Zatsepin et al., Bioconjugate Chemistry 13 :822 (2002).*

(Continued)

*Primary Examiner* — Ethan C Whisenant
(74) *Attorney, Agent, or Firm* — John P. White; Gary J. Gershik; Cooper & Dunham LLP

(57) ABSTRACT

This invention provides methods for detecting the presence of a plurality of predetermined compounds in a sample using a plurality of tag moieties and at least one nanopore. This invention also provides methods for determining the quantity of each of a plurality of predetermined compounds in a sample using a plurality of tag moieties and at least one nanopore. This invention further provides methods for detecting interaction of at least two predetermined compounds using at least one tag moiety and at least one nanopore.

25 Claims, 7 Drawing Sheets

(56) References Cited

U.S. PATENT DOCUMENTS

| | | | |
|---|---|---|---|
| 7,713,698 B2 | 5/2010 | Ju et al. |
| 7,745,116 B2 | 6/2010 | Williams |
| 7,777,505 B2 | 8/2010 | White et al. |
| 7,790,869 B2 | 9/2010 | Ju et al. |
| 7,871,777 B2 | 1/2011 | Schneider et al. |
| 7,883,869 B2 | 2/2011 | Ju et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,982,029 B2 | 7/2011 | Ju et al. |
| 8,088,575 B2 | 1/2012 | Ju et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,298,792 B2 | 10/2012 | Ju et al. |
| 8,541,849 B2 | 9/2013 | Chen et al. |
| 8,652,779 B2 | 2/2014 | Turner et al. |
| 8,796,432 B2 | 8/2014 | Ju et al. |
| 8,889,348 B2 | 11/2014 | Ju |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 2003/0027140 A1 | 2/2003 | Ju et al. |
| 2003/0101006 A1 | 5/2003 | Mansky et al. |
| 2004/0038215 A1* | 2/2004 | Kumar .................. C07H 19/04 435/6.18 |
| 2005/0186576 A1 | 8/2005 | Chan et al. |
| 2005/0208574 A1 | 9/2005 | Bayley et al. |
| 2006/0057565 A1 | 3/2006 | Ju et al. |
| 2006/0105461 A1 | 5/2006 | Tom-Moy et al. |
| 2006/0115951 A1 | 6/2006 | Mosley |
| 2006/0252038 A1 | 11/2006 | Ju et al. |
| 2007/0190542 A1 | 8/2007 | Ling et al. |
| 2007/0190543 A1* | 8/2007 | Livak .................. C12Q 1/6816 435/6.19 |
| 2008/0101988 A1 | 5/2008 | Kang et al. |
| 2008/0199932 A1 | 8/2008 | Hanzel et al. |
| 2008/0218184 A1 | 9/2008 | White et al. |
| 2009/0029477 A1 | 1/2009 | Meller et al. |
| 2009/0054919 A2* | 2/2009 | Winters-Hilt .... A61B 17/32093 606/172 |
| 2009/0066315 A1 | 3/2009 | Hu et al. |
| 2009/0073293 A1 | 3/2009 | Yaffe et al. |
| 2009/0081711 A1* | 3/2009 | Singh .................. G01N 33/564 435/7.25 |
| 2009/0087834 A1 | 4/2009 | Lexow et al. |
| 2009/0099786 A1 | 4/2009 | Oliver et al. |
| 2009/0136958 A1 | 5/2009 | Gershow et al. |
| 2009/0167288 A1 | 7/2009 | Reid et al. |
| 2009/0240030 A1 | 9/2009 | Ju et al. |
| 2009/0298075 A1* | 12/2009 | Travers ................ C12Q 1/6869 435/6.12 |
| 2009/0325154 A1 | 12/2009 | Ju |
| 2010/0025238 A1 | 2/2010 | Gottlieb et al. |
| 2010/0025249 A1 | 2/2010 | Polonsky et al. |
| 2010/0035260 A1 | 2/2010 | Olasagasti et al. |
| 2010/0072080 A1 | 3/2010 | Karhanek et al. |
| 2010/0075328 A1 | 3/2010 | Bjornson et al. |
| 2010/0148126 A1 | 6/2010 | Guan et al. |
| 2010/0227414 A1 | 9/2010 | Ervin |
| 2010/0243449 A1 | 9/2010 | Oliver |
| 2010/0261247 A1 | 10/2010 | Hanzel et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014611 A1 | 1/2011 | Ju et al. |
| 2011/0039259 A1 | 2/2011 | Ju et al. |
| 2011/0168968 A1 | 7/2011 | Yang et al. |
| 2011/0174625 A1 | 7/2011 | Akeson et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0287414 A1 | 11/2011 | Chen et al. |
| 2012/0052188 A1 | 3/2012 | Chen et al. |
| 2012/0094278 A1 | 4/2012 | Akeson et al. |
| 2012/0115736 A1 | 5/2012 | Bjornson et al. |
| 2012/0142006 A1 | 6/2012 | Ju et al. |
| 2012/0142088 A1* | 6/2012 | Hsiao ................ A61K 47/6901 435/325 |
| 2012/0156680 A1 | 6/2012 | Ju et al. |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0214162 A1 | 8/2012 | Oliver |
| 2012/0261261 A1 | 10/2012 | Huber |
| 2013/0071837 A1* | 3/2013 | Winters-Hilt ........ C12Q 1/6869 435/6.11 |
| 2013/0244340 A1* | 9/2013 | Davis ................ G01N 33/48721 436/501 |
| 2013/0244886 A1* | 9/2013 | Rigatti .................. C12Q 1/6806 506/2 |
| 2013/0260371 A1* | 10/2013 | Holt .................. G01N 33/48721 435/6.1 |
| 2013/0264207 A1 | 10/2013 | Ju et al. |
| 2013/0280700 A1 | 10/2013 | Ju et al. |
| 2014/0034497 A1 | 2/2014 | Davis et al. |
| 2014/0093869 A1 | 4/2014 | Ju et al. |
| 2014/0174927 A1* | 6/2014 | Bashir .................. C12Q 1/6827 204/452 |
| 2014/0206553 A1 | 7/2014 | Ju et al. |
| 2014/0309129 A1* | 10/2014 | Gu .................. G01N 33/48721 506/9 |
| 2014/0315191 A1 | 10/2014 | Ju et al. |
| 2014/0377743 A1 | 12/2014 | Ju et al. |
| 2015/0037788 A1 | 2/2015 | Ju et al. |
| 2015/0080232 A1 | 3/2015 | Ju et al. |
| 2015/0111759 A1 | 4/2015 | Ju et al. |
| 2015/0119259 A1 | 4/2015 | Ju et al. |
| 2015/0368710 A1 | 12/2015 | Fuller et al. |
| 2016/0041179 A1 | 2/2016 | Ju et al. |

FOREIGN PATENT DOCUMENTS

| | | |
|---|---|---|
| WO | WO 02/22883 A1 | 3/2002 |
| WO | WO 02/29003 | 4/2002 |
| WO | WO 02/79519 A1 | 10/2002 |
| WO | WO 07/53702 | 5/2007 |
| WO | WO0762105 | 5/2007 |
| WO | WO2007127327 | 11/2007 |
| WO | WO2008102120 | 8/2008 |
| WO | WO2008124107 | 10/2008 |
| WO | WO2009007743 | 1/2009 |
| WO | WO2009020682 | 2/2009 |
| WO | WO2010109197 | 9/2010 |
| WO | WO 2011/097028 A1 | 8/2011 |
| WO | WO2011106459 | 9/2011 |
| WO | WO2012009578 | 1/2012 |
| WO | WO 2012/162429 | 11/2012 |
| WO | WO2013016486 | 1/2013 |
| WO | WO2013123450 | 8/2013 |
| WO | WO 2013/154999 | 10/2013 |
| WO | WO 2013/191793 | 12/2013 |
| WO | WO2013188841 | 12/2013 |
| WO | WO 2014/144883 | 9/2014 |
| WO | WO 2014/144898 | 9/2014 |
| WO | WO 2015/123430 | 8/2015 |

OTHER PUBLICATIONS

Barbee et al., Multiplexed protein detection using antibody-conjugated microbead arrays in a microfabricated electrophoretic device. Lab on a Chip 10:3084 (2010). (Year: 2010).*

Dela Torre et al., Fabrication and characterization of solid-state nanopore arrays for high-throughput DNA sequencing. Nanotechnology 23 : 385308 (2012) 6 pgs. (Year: 2012).*

(56) References Cited

OTHER PUBLICATIONS

Kim et al., Rapid Fabrication of Uniformly Sized Nanopores and Nanopore Arrays for Parallel DNA Analysis. Advanced Materials 18 :33149(2006) (Year: 2006).*
Patterson et al., Combinatorics and next-generation sequencing. Nature Biotechnology 27 (9) : 826 (2009). (Year: 2009).*
Venkatesan et al., Nanopore sensors for nucleic acid analysis. Nature Nanotechnology 6: 615 (2011). (Year: 2011).*
Actis et al., Immunoassays using Artifical Nanopore. wwwintechopen. com (Year: 2013).*
Rotem et al., Protein Detection by Nanopores Equipped with Aptamers. JACS 134 : 2781 (Year: 2012).*
Actis et al., Immunoassays using artificial nanopores. WWW.inotech. com (Year: 2012).*
Atlas et al., DNA sequencing and bar-coding using solid-state nanopores. Electrophoresis 33 : :3437 (Year: 2012).*
De la Escsura-Muniz et al., A Nanochannel/Nanoparticle-based Filtering and Sensing Platform for direct detection of a cancer biomarker in blood. Small 7(5) : 675 (Year: 2011).*
Gyurcsanyl, RE. Chemically-modified nanopores for sensening (Year: 2009).*
Han et al., Label-Free Detection of Single Protein Molecules and Protein-Protein Interactions Using Synthetic Nanopores. Analytical Chjemistry 80:4651-4658 (Year: 2008).*
Iqbal et al., Solid-state nanopore channels with DNA selectivity. Nature Nanotechnology 2 :243 (Year: 2007).*
Kim et al.,Nanopore membrane-based electrochemical immunoassay. J. Solid State Electrochem. 13:1037-1042 (Year: 2009).*
Lin et al., Immunoassay channels for—fetoprotein based on encapsulation of biorecognition molecules into SBA-15 mesopores. Analytica Chimica Acta 643 :90-94 (Year: 2009).*
Liu et al.,Two-Way Nanopore Sensing of Sequence-Specific Oligonucleotides and Small-Molecule Targets in Complex Matrices Using Integrated DNA Supersandwich Structures. Agnew. Chem. Int. Ed. 52:2007 (Jan. 2013) (Year: 2013).*
Movileanu, L. Interrogating single proteins through nanopores: challenges and opportunities. Trends in Biotechnology 27(6) :333 (Year: 2009).*
Nguyen et al., Membrane-Based Electrochemical Nanobiosensor for the Detection of Virus. Analytical XChemistry 81 : 7226-7234 (Year: 2009).*
Sexton et al., Resistive-Pulse Studies of Proteins and Protein/ Antibody Complexes Using a Conical Nanotube Sensor. JACS 129 :13144 (Year: 2007).*
Umehara et al., Label-free biosensing with functionalized nanopipette probes. PNAS 106(12) :4611-4616 (Year: 2009).*
Wang and Smirnov.Label-Free DNA Sensor Based on Surface Charge Modulated Ionic Conductance. ACSNano 3(4) : 1004 (Year: 2009).*
Yang et al., Streptavidin-Functionalized Three-Dimensional Ordered Nanoporous Silica Film for Highly Efficient Chemiluminescent Immunosensing. Advanced Functional Materials 18 :3991-3998 (Year: 2008).*
International Search Report and Written Opinion of the International Searching Authority issued by the International Searching Authority (ISA/US) dated Oct. 29, 2007 in connection with International Application No. PCT/US2007/013559.
International Preliminary Report on Patentability, dated Dec. 10, 2008 in connection with International Application No. PCT/US2007/ 013559.
Jun. 23, 2011 Restriction Requirement issued in connection with U.S. Appl. No. 12/308,091.
Oct. 24, 2011 Response to Restriction Requirement dated Jun. 23, 2011 in connection with U.S. Appl. No. 12/308,091.
Office Action dated Nov. 29, 2011 in connection with U.S. Appl. No. 12/308,091.
Jun. 22, 2011 Office Action in connection with Chinese Patent Application No. 200780028545.1 (with English translation of cover page only).

International Search Report and the Written Opinion of the International Searching Authority, or the Declaration, including an International Search Report and Written Opinion of the International Searching Authority, dated Feb. 4, 2013 in connection with PCT International Application No. PCT/US2011/065640, filed Dec. 16, 2011.
Jan. 6, 2012 Response to First Office Action filed in connection with Chinese Patent Application No. 200780028545.1 (with English translation).
Apr. 30, 2012 Amendment in Response to Office Action dated Nov. 29, 2011 in connection with U.S. Appl. No. 12/308,091.
Jun. 28, 2012 Office Action issued in connection with U.S. Appl. No. 12/308,091.
Jul. 2, 2012 Second Office Action in connection with Chinese Patent Application No. 200780028545.1 (with English translation.
Nov. 19, 2012 Response to Second Office Action filed in connection with Chinese Patent Application No. 200780028545.1 (with English translation).
Dec. 28, 2012 Amendment in Response to Office Action dated Nov. 29, 2011 in connection with U.S. Appl. No. 12/308,091.
Apr. 9, 2013 Third Office Action in connection with Chinese Patent Application No. 200780028545.1 (with English translation).
Jun. 21, 2013 Response to Third Office Action filed in connection with Chinese Patent Application No. 200780028545.1.
Invitation to Pay Additional Fees mailed by the International Searching Authority dated Aug. 19, 2013 connection with PCT International Application No. PCT/US2013/035635.
International Search Report and Written Opinion of the International Searching Authority dated Sep. 24, 2013 in connection with PCT International Application No. PCT/US2013/035630.
Oct. 12, 2013 Decision of Rejection issued in connection with Chinese Patent Application No. 200780028545.1.
International Search Report and Written Opinion of the International Searching Authority dated Oct. 25, 2013 in connection with PCT International Application No. PCT/US2013/035635.
Jan. 26, 2014 Request for Reexamination filed in connection with Chinese Patent Application No. 200780028545.1.
Apr. 16, 2014 Communication transmitting Supplementary European Search Report and European Search Opinion in connection with European Patent Application No. EP 11848220.
Mar. 27, 2014 Office Action in connection with Chinese Patent Application No. 201180063978.7 (with English translation).
Jul. 17, 2014 Notice of Allowance issued in connection with U.S. Appl. No. 12/308,091.
International Search Report and Written Opinion of the International Searching Authority dated Jul. 30, 2014 in connection with PCT International Application No. PCT/US2014/029495.
Aug. 11, 2014 Response dated Mar. 27, 2014 Office Action in connection with Chinese Patent Application No. 201180063978.7 (with English translation of cover page only).
Oct. 22, 2014 Amendment in response dated May 22, 2014 Notice of Missing Requirements in connection with U.S. Appl. No. 13/994,431.
Nov. 14, 2014 Response dated Apr. 16, 2014 Communication transmitting Supplementary European Search Report and European Search Opinion in connection with European Patent Application No. EP 11848220.7.
Dec. 22, 2014 Second Office Action in connection with Chinese Patent Application No. 201180063978.7 (with English translation of cover page only).
Dec. 23, 2014 Communication pursuant to Article 94(3) EPC in connection with European Patent Application No. EP 11848220.7.
Preliminary Amendment filed Feb. 17, 2015 in connection with U.S. Appl. No. 13/994,431.
Mar. 6, 2015 Response dated Dec. 22, 2014 Second Office Action in connection with Chinese Patent Application No. 201180063978. 7.
Mar. 24, 2015 Office Action issued in connection with Chinese Patent Application No. 200780028545.1.
May 4, 2015 Amendment in response dated Dec. 23, 2014 Communication pursuant to Article 94(3) EPC in connection with European Patent Application No. EP 11848220.7.

(56) References Cited

OTHER PUBLICATIONS

Jul. 13, 2015 Third Office Action in connection with Chinese Patent Application No. 201180063978.7 (with English translation of cover page.
Jul. 15, 2015 Communication pursuant to Article 94(3) EPC in connection with European Patent Application No. EP 11848220.7.
International Search Report and Written Opinion of the International Searching Authority dated Jun. 29, 2015 in connection with PCT International Application No. PCT/US2015/022063.
Office Action dated Jul. 15, 2015 by the Chinese State Intellectual Property Office in connection with Chinese Patent Application No. 201380025837.5.
Aug. 5, 2015 Applicant Statement in connection with U.S. Appl. No. 14/666,124 regarding Amendments to p. 40 Regarding Tagged Nucleotides.
International Search Report and Written Opinion of the International Searching Authority dated Aug. 25, 2015 in connection with PCT International Application No. PCT/US2015/015647.
Sep. 28, 2015 Response dated Mar. 24, 2015 Office Action issued in connection with Chinese Patent Application No. 200780028545.1 (English translation of coversheet).
Nov. 13, 2015 Decision on Reexamination issued in connection with Chinese Patent Application No. 200780028545.1.
Communication pursuant to Rule 164(1) EPC dated Dec. 2, 2015 by the EPO in connection with EP 13807639.3.
Communication pursuant to Rule 164(1) EPC dated Dec. 7, 2015 by the EPO in connection with EP 13775787.8.
Jan. 15, 2016 Communication Pursuant to Article 94(3) EPC in connection with European Patent Application No. EP 11848220.7.
Jan. 29, 2016 Office Action issued in connection with Chinese Patent Application No. 200780028545.1.
Response to the Jul. 15, 2015 Office Action, filed Jan. 29, 2016 in connection with Chinese Patent Application No. 201380025837.5.
Feb. 3, 2016 Office Action issued in connection with Chinese Patent Application No. 200780028545.1.
Extended European Search Report dated Mar. 11, 2016 by the EPO in connection with EP 13775787.8.
Extended European Search Report dated Mar. 11, 2016 by the EPO in connection with EP 13807639.3.
Voluntary Amendment filed Mar. 17, 2016 in connection with Chinese Patent Application No. CN 2014800159374.
Anderson, Sequencing and the single channel. Biophys J. Dec. 1999; 77(6):2899-901.
Ashkenasy et al. Recognizing a single base in an individual DNA strand: a step toward DNA sequencing in nanopores. Angew Chem Int Ed Engl. Feb. 18, 2005; 44(9):1401-4.
Atanasnov et al. Membrane on a chip: a functional tethered lipid bilayer membrane on silicon oxide surfaces. Biophys J. Sep. 2005; 89(3):1780-8.
Benner, et al. Sequence-specific detection of individual DNA polymerase complexes in real time using a nanopore. Nat Nanotechnol. Nov. 2007; 2(11):718-24. Epub Oct. 28, 2007.
Bezrukov, S.M., and Kasianowicz, J.J. (2001) "Neutral Polymers in the nanopores of alamethicin and alpha-hemolysin." Biologicheskie Membrany 18:451-455.
Bokhari, S.H. et al. (2005) "A Parallel Graph Decomposition Algorithm for DNA Sequencing with Nanopores" Bioinformatics 21(7):889-896.
Buchmann, et al. Electrochemical release from gold-thiolate electrodes for controlled insertion of ion channels into bilayer membranes. Bioorg Med Chem. Mar. 15, 2004; 12(6):1315-24.
Butler, et al. Determination of RNA orientation during translocation through a biological nanopore. Biophys J. Jan. 1, 2006; 90(1):190-9. Epub Oct. 7, 2005.
Butler, et al. Ionic current blockades from DNA and RNA molecules in the alpha-hemolysin nanopore. Biophys J. Nov. 1, 2007; 93(9):3229-40. Epub Aug. 3, 2007.

Chandler, E.L et al. (2004) "Membrane Surface Dynamics of DNA-Threaded Nanopores Revealed by Simultaneous Single-Molecule Optical and Ensemble Electrical Recording." Langmuir 20:898-905.
Clarke, et al. "Continuous base identification for single-molecule nanopore DNA sequencing" Nat Nanotechnol. Apr. 2009; 4(4):265-70. Epub Feb. 22, 2009.
Cockroft, et al. A single-molecule nanopore device detects DNA polymerase activity with single-nucleotide resolution. J Am Chem Soc. Jan. 23, 2008; 130(3):818-20. Epub Jan. 1, 2008.
Danleon, et al. Cell membranes suspended across nanoaperture arrays. Langmuir. Jan. 3, 2006; 22(1):22-5.
Deamer, D.W. et al (2002) "Characterization of nucleic acids by nanopore analysis." Acc. Chem. Res. 35(10):817-825.
Eid et al. (2009) "Real-Time DNA Sequencing from Single Polymerase Molecules", Science, 23(5910):133-138.
Ervin, et al. Simultaneous alternating and direct current readout of protein ion channel blocking events using glass nanopore membranes. Anal Chem. Mar. 15, 2008; 80(6):2069-76. Epub Feb. 23, 2008.
Fologea, D. et al. (2005) "Slowing DNA Translocation in a Solid State Nanopore" Nano Letters 5(9), 1734-1737.
Fologea, D. et al. (2005) "Detecting Single Stranded DNA with a Solid State Nanopore" Nano Letters 5(10):1905-1909.
Heng, J.B. et al. (2005) "Stretching DNA Using the Electric Field in a Synthetic Nanopore" Nano Letters 5(9):1734-1737.
Heng, J.B. et al. (2006) "The Electromechanics of DNA in a synthetic nanopore" Biophysical Journal 90:1098-1106.
Henrickson, S.E. et al (2000) "Driven DNA Transport into an Asymmetric Nanometer-scale Pore" Physical Review Letters 85:3057-3060.
Holden, et al. Direct introduction of single protein channels and pores into lipid bilayers. J Am Chem Soc. May 11, 2005; 127(18):6502-3.
Holden, et al. Direct transfer of membrane proteins from bacteria to planar bilayers for rapid screening by single-channel recording. Nat Chem Biol. Jun. 2006; 2(6):314-8. Epub May 7, 2006.
Hromada, et al. Single molecule measurements within individual membrane-bound ion channels using a polymer-based bilayer lipid membrane chip. Lab Chip. Apr. 2008; 8(4):602-8. Epub Feb. 29, 2008.
Kang et al. A storable encapsulated bilayer chip containing a single protein nanopore. J Am Chem Soc. Apr. 18, 2007; 129(15):4701-5. Epub Mar. 22, 2007.
Kasianowicz J.J., Brandin, B., Branton, D. and Deamer, D.W. (1996) "Characterization of Individual Polynucleotide Molecules Using a Membrane Channel," Proc. Natl. Acad. Sci. USA 93:13770-13773.
Kasianowicz, J.J. (2003) "Nanonmeter-scale pores: potential applications for DNA characterization and analyte detection." Disease Markers 18:185-191.
Kasianowicz J.J. (2004) "Nanopore. Flossing with DNA" Nature Materials 3:355-356.
Kawano et al. Controlling the translocation of single-stranded DNA through alpha-hemolysin ion channels using viscosity. Langmuir. Jan. 20, 2009; 25(2):1233-7.
Kumar et al. PEG-labeled nucleotides and nanopore detection for single molecule DNA sequencing by synthesis. Sci Rep. 2012; 2:684. Epub Sep. 21, 2012.
Kutik et al. Dissecting membrane insertion of mitochondrial beta-barrel proteins. Cell. Mar. 21, 2008; 132(6):1011-24.
Li. L. et al. (2001) "Ion-beam sculpting at nanometre length scales" Nature 412:166-169.
Lieberman et al. "Processive Replication of Single DNA Molecules Catalyzed by phi29 DNA Polymerase", Jol. ACS, vol. 132, No. 50, Dec. 22, 2010, pp. 17961-17972.
Madampage, et al. Nanopore detection of antibody prion interactions. Anal Biochem. Jan. 1, 2010; 396(1):36-41. Epub Aug. 21, 2009.
Mathe, J. et al. (2004) "Nanopore Unzipping of Individual Hairpin Molecules" Biophysical Journal 87:3205-3212.

(56) References Cited

OTHER PUBLICATIONS

Mauer et al. Reconstitution of ion channels in agarose-supported silicon orifices. Biosens Bioelectron. May 15, 2007; 22(11):2577-84. Epub Nov. 13, 2006.

McNally et al. Optical recognition of converted DNA nucleotides for single-molecule DNA sequencing using nanopore arrays. Nano Lett. Jun. 9, 2010; 10(6):2237-44.

Meller, A. et al. (2000) "Rapid nanopore discrimination between single polynucleotide molecules." Proc. Natl. Acad. Sci. USA 97:1079-1084.

Meller, A. et al. (2002) "Single Molecule Measurements of DNA Transport Through a Nanopore" Electrophoresis 23:2583-2591.

Mohammad et al. Controlling a single protein in a nanopore through electrostatic traps. J Am Chem Soc. Mar. 26, 2008; 130(12):4081-8. Epub Mar. 6, 2008.

Nakane et al. A Nanosensor for Transmembrane Capture and Identification of Single Nucleic Acid Molecules, Biophysical Journal, vol. 87, Issue 1, Jul. 2004, pp. 615-621, ISSN 0006-3495.

Oxford Nanopore Technologies, Sensor Array Chip, Jul. 14, 2011.

Park et al. DNA hybridization sensors based on electrochemical impedance spectroscopy as a detection tool. Sensors (Basel). 2009; 9(12):9513-32. Epub Nov. 26, 2009.

Purnell et al. Discrimination of single base substitutions in a DNA strand immobilized in a biological nanopore. ACS Nano. Sep. 22, 2009; 3(9):2533-8.

Robertson et al., (2007) "Single-Molecule Mass Spectrometry in Solution Using a Solitary Nanopore" PNAS, 104(20):8207-8211.

Rothberg, J.M. et al. (2011) "An integrated semiconductor device enabling non-optical genome sequencing" Nature 475:348-352.

Sanchez-Magraner, et al. Membrane insertion of *Escherichia coli* alpha-hemolysin is independent from membrane lysis. J Biol Chem. Mar. 3, 2006; 281(9):5461-7. Epub Dec. 22, 2005.

Sauer-Budge, A.F. et al. (2003) "Unzipping Kinetics of Double Stranded DNA in a Nanopore" Physical Review Letters 90(23):238101-1-238101-4.

Seo et al., (2004) "Photocleavable Fluorescent Nucleotides for DNA Sequencing on a Chip Constructed by Site-Specific Coupling Chemistry," PNAS 101(15):5488-5493.

Shim et al., Encapsulating a single G-quadruplex aptamer in a protein nanocavity. J Phys Chem B. Jul. 17, 2008; 112(28):8354-60. Epub Jun. 19, 2008.

Simon et al., Formation and stability of a suspended biomimetic lipid bilayer on silicon submicrometer-sized pores. J Colloid Interface Sci. Apr. 15, 2007; 308(2):337-43. Epub Jan. 31, 2007.

Singer et al. Nanopore Based Sequence Specific Detection of Duplex DNA for Genomic Profiling, Jan. 8, 2010, published Jan. 20, 2010, pp. 738-742.

Sterfureac et al. Transport of alpha-helical peptides through alpha-hemolysin and aerolysin pores. Biochemistry. Aug. 1, 2006; 45(30):9172-9.

Stefureac et al. Nanopore analysis of the interaction of metal ions with prion proteins and peptides. Biochem Cell Biol. Apr. 2010; 88(2):347-58.

Stoddart et al. Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Stoddart et al. Nucleobase recognition in ssDNA at the central constriction of the alpha-hemolysin pore. Nano Lett. Sep. 8, 2010; 10(9):3633-7.

Studer et al., Formation of individual protein channels in lipid bilayers suspended in nanopores. Colloids Surf B Biointerfaces., Oct. 15, 2009; 73(2):325-31. Epub Jun. 10, 2009.

Suzuki et al., Highly reproducible method of planar lipid bilayer reconstitution in polymethyl methacrylate microfluidic chip. , Feb. 2006, Langmuir. 22(4):1937-42.

Thomson et al., Preliminary nanopore cheminformatics analysis of aptamer-target binding strength, Nov. 2007, BMC Bioinformatics. 1; 8 Suppl 7:S11.

Vercoutere W. et al., "Rapid discrimination among individual DNA hairpin molecules at single-nucleotide resolution using an ion channel.", 2001, Nat. Biotech 19:248-252.

Viasnoff et al., Probing DNA base pairing energy profiles using a nanopore. Eur Biophys J., Feb. 2009, 38(2):263-9. Epub Oct. 3, 2008.

Wanunu et al., DNA profiling using solid-state nanopores: detection of DNA-binding molecules. Nano Lett. Oct. 2009; 9(10):3498-502.

Wei et al.,"Stochastic sensing of proteins with receptor-modified solid-state nanopores" Nature Nanotechnology, 7(4):257-263 (2012).

Weng et al., Fluid biomembranes supported on nanoporous aerogel/xerogel substrates. Langmuir. Aug. 17, 2004; 20(17):7232-9.

Wilson et al., Feedback control of a DNA molecule tethered in a nanopore to repeatedly probe DNA-binding enzymes. Conf Proc IEEE Eng Med Biol Soc. 2008; 2008:5745-8.

Winters-Hilt et al., Nanopore-based kinetics analysis of individual antibody-channel and antibody-antigen interactions. BMC Bioinformatics. Nov. 1, 2007; 8 Suppl 7:S20.

Wu et al., Single-molecule detection of nitrogen mustards by covalent reaction within a protein nanopore. J Am Chem Soc. May 28, 2008; 130(21):6813-9. Epub Apr. 30, 2008.

Zeineldin et al., Using bicellar mixtures to form supported and suspended lipid bilayers on silicon chips. Langmuir. Sep. 12, 2006; 22(19):8163-8.

Zwolak, et al. Electronic signature of DNA nucleotides via transverse transport. Nano Lett. Mar. 2005; 5(3):421-4.

\* cited by examiner

Coumarin-PEG16-NH$_2$

Coumarin-PEG20-NH$_2$

Coumarin-PEG24-NH$_2$

Coumarin-PEG36-NH$_2$

METHOD FOR DETECTING MULTIPLE PREDETERMINED COMPOUNDS IN A SAMPLE

CROSS-REFERENCE TO RELATED APPLICATIONS

This application is a § 371 national stage of PCT International Application No. PCT/US2014/029495, filed Mar. 14, 2014, claiming the benefit of U.S. Provisional Application No. 61/799,276, filed Mar. 15, 2013, the contents of each of which are hereby incorporated by reference in their entirety.

Throughout this application, certain patents and publications are referenced, the latter by authors and publication year. Full citations for these publications may be found immediately preceding the claims. The disclosures of these patents and publications in their entireties are hereby incorporated by reference into this application in order to describe more fully the state of the art to which this invention relates.

FIELD OF INVENTION

This invention provides methods for detecting the presence of a plurality of predetermined compounds in a sample using a plurality of tag moieties and at least one nanopore. This invention also provides methods for determining the quantity of each of a plurality of predetermined compounds in a sample using a plurality of tag moieties and at least one nanopore. This invention further provides methods for detecting interaction of at least two predetermined compounds using a tag moiety and at least one nanopore.

BACKGROUND OF THE INVENTION

Classic immunological approaches to detection of proteins using antibodies, receptors, or other binding partners include, among others, enzyme-linked immunosorbent (ELISA) assay (generally in the form of an antibody sandwich method), radioimmunoassays, and immunoblotting methods (Burnette 1981, Engvall at al. 1971, and Yalow et al. 19601, with equivalent biochemical approaches being used for protein-receptor and protein-ligand reactions. Majority of these methods rely on examining one protein at a time. Moreover, the protein target typically must be present in large amounts and at relatively high concentrations to assure a reliably detectable signal.

Beginning in 1975 but largely over the last 15 years, methods that attempt to simultaneously examine many different proteins have appeared. These include 2-D gel electrophoresis, tandem mass spectrometry (MS-2 or MS-3) systems with intermediate protein cleavage, isotope-coded affinity tag (ICAT)-MS, MudPIT (LC-2/MS-2), and combinations of these approaches [Guerrera et al. 2005, Gygi et al. 1999, Klose 1975, and O'Farrell 1975]. For instance, in the ICAT approach, proteins from different tissues are labeled with tags containing either hydrogen or deuterium, and the differential patterns are observed by mass spectrometry. While many of these methods allow multiple samples to be compared concurrently, due to the cost of associated technologies such as mass spectroscopy, many of these approaches have not found general utility.

A relatively recent addition to the repertoire, protein arrays, in which fluorescently labeled proteins are allowed to bind to numerous spots, each containing covalently attached antibodies for a specific protein (antigen), are an appealing solution, as they can be mass produced and data analysis standardized [Angenendt 2005, Bussow at al. 1998, Cahill 2001, de Wildt at al. 2000]. While limited by the number of available specific antibodies that can function on a solid phase, a more important shortcoming of this method is the relative binding ability of the antibodies. Unlike DNA probes on gene expression microarrays, where probes can be selected to be fairly uniform in their binding affinity for mRNA targets, different antibodies may bind their fluorescently labeled antigens with very different affinities. Because of this variable affinity, quantification from spot to spot (antigen to antigen) becomes difficult, especially when combined with the likelihood that the fluorescent signal can lie outside of the linear range of detection. For example, low copy number proteins in the sample will not be seen, unless their binding is stronger than the average antigen-antibody interaction elsewhere on the chip, in which case they will be over-represented. Moreover, the effective concentration range will have the same floors and ceilings as other fluorescent methods on microarrays, and small changes in protein levels will be difficult to distinguish using protein arrays. Another common issue with fluorescent labeling is the existence of overlapping emission spectra, which limits the number of differentially labeled samples that can be applied to the arrays.

In summary, gene regulation analysis at the level of protein synthesis, like proteomics in general, lags behind nucleic acid analysis in its throughput, sensitivity and automation. This is due to the relatively poor stability of proteins, their high heterogeneity, and the requirement for a much wider dynamic range of detection with increased demand for sensitivity approaching the single molecule detection level, a need not easily met by fluorescent or colorimetric measurements. While protein arrays based on antibody interactions with fluorescently labeled antigens or secondary antibodies have gained some degree of popularity over the last decade [Cahill 2001], some of the drawbacks of this approach, including fluorescence saturation and overlap in fluorescent emission, make accurate quantification difficult. While there are currently several examples of application of nanopore-based analytics, no existing technology allows quantification of protein-protein interactions with a plurality of tags.

SUMMARY OF THE INVENTION

This invention provides a method for detecting the presence of a plurality of predetermined compounds in a sample which comprises:
(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;
(b) treating the sample from step (a) to form an electrolyte solution containing the detectably tagged predetermined compounds;
(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore;

(d) treating the detectably tagged predetermined compounds bound to said at least one nanopore so as to separate the tag moieties from the predetermined compounds; and (e) detecting said at least one detectable component of each of the tag moieties so released as the tag moieties pass through said at least one nanopore so as to thereby detecting the presence of the plurality of predetermined compounds in the sample.

This invention provides a method for detecting the presence of a plurality of predetermined compounds in a sample which comprises:

(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore, and wherein each of the tag moieties of said bound detectably tagged predetermined compounds localizes within said at least one nanopore;

(d) detecting said at least one detectable component of each of the tag moieties with said at least one nanopore so as to thereby detecting the presence of the plurality of predetermined compounds in the sample.

This invention also provides a method for determining the quantity of each of a plurality of predetermined compounds in a sample which comprises:

(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore;

(d) treating the detectably tagged predetermined compounds bound to said at least one nanopore so as to separate the tag moieties from the predetermined compounds;

(e) determining the amount of said at least one detectable component of each of the tag moieties so released as the tag moieties pass through said at least one nanopore; and (f) determining, from the amounts of said detectable components determined in step (e), the quantity of each of the plurality of predetermined compounds present in the sample.

This invention also provides a method for determining the quantity of each of a plurality of predetermined compounds in a sample which comprises:

(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore, and wherein each of the tag moieties of said bound detectably tagged predetermined compounds localizes within said at least one nanopore;

(d) determining the amount of said at least one detectable component of each of the tag moieties with said at least one nanopore; and (e) determining, from the amounts of said detectable components determined in step (d), the quantity of each of the plurality of predetermined compounds present in the sample.

This invention further provides a method for detecting interaction of at least two predetermined compounds which comprises:

(a) contacting at least a first predetermined compound present in a sample with a detectable tag moiety, wherein the detectable tag moiety comprises at least one detectable component, under conditions permitting the tag moiety to attach to the predetermined compound present in the sample to form a detectably tagged predetermined compound;

(b) treating the sample from step (a) to form an electrolyte solution containing the detectably tagged predetermined compounds;

(c) contacting the electrolyte solution from step (b) with at least one nanopore, wherein at least a second predetermined compound is immobilized on said at least one nanopore, under conditions permitting the binding of the detectably tagged predetermined compound with the second predetermined compound;

(d) treating the detectably tagged predetermined compound bound to said at least one nanopore so as to separate the tag moiety from the predetermined compound; and (e) detecting said at least one detectable component of the tag moiety so released as the tag moiety passes through said at least one nanopore so as to thereby detecting the interaction of the predetermined compounds.

This invention even further provides a method for detecting interaction of at least two predetermined compounds which comprises:
(a) contacting at least a first predetermined compound present in a sample with a detectable tag moiety, wherein the detectable tag moiety comprises at least one detectable component, under conditions permitting the tag moiety to attach to the predetermined compound present in the sample to form a detectably tagged predetermined compound;
(b) treating the sample from step (a) to form an electrolyte solution containing the detectably tagged predetermined compound;
(c) contacting the electrolyte solution from step (b) with at least one nanopore, wherein at least a second predetermined compound is immobilized on said at least one nanopore, under conditions permitting the binding of the detectably tagged predetermined compound with the second predetermined compound, and wherein the tag moiety of said detectably tagged predetermined compound bound to the second predetermined compound localizes within said at least one nanopore;
(d) detecting said at least one detectable component of the tag moiety with said at least one nanopore so as to thereby detecting the interaction of the predetermined compounds.

This invention even further provides a method for detecting the presence of a plurality of predetermined compounds in a plurality of samples, comprising:
(a) contacting each sample with a nanopore-detectable tag moiety, under conditions permitting the tag moiety to attach to the plurality of predetermined compounds present in the sample to form detectably tagged predetermined compounds for that sample, which are distinguishable from any nanopore-detectable tag moiety attached to similar predetermined compounds from any other sample;
(b) mixing the resulting tagged compounds from the plurality of samples from step (a) and treating them in such a way as to form an electrolyte solution containing the set of detectably and distinguishably tagged predetermined compounds;
(c) contacting the electrolyte solution from step (b) with at least one nanopore, wherein said at least one nanopore comprises a means for specific analyte moiety binding to each of the detectably tagged predetermined compounds in the electrolyte solution, under conditions such that the detectably tagged predetermined compounds bind to said at least one nanopore;
(d) treating the detectably tagged predetermined compounds bound to said at least one nanopore so as to separate the tag moieties from the predetermined compounds; and
(e) detecting said at least one detectable component of each of the tag moieties so released as the tag moieties pass through said at least one nanopore so as to thereby detect the presence of the plurality of predetermined compounds in the plurality of samples.

DETAILED DESCRIPTION OF THE INVENTION

Figure 1:
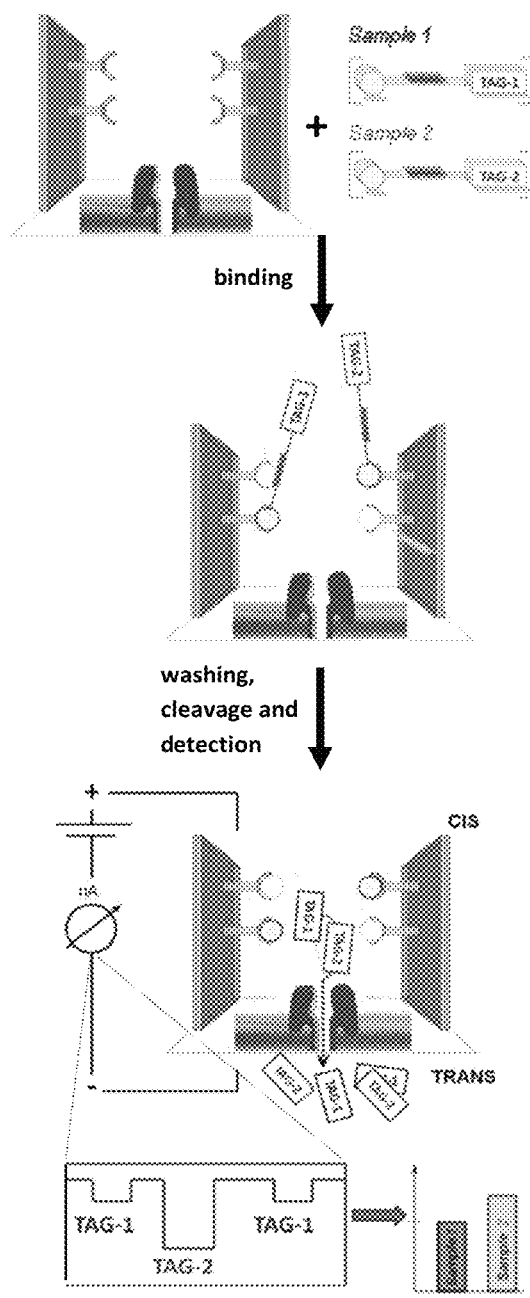
FIG. 1. Multiplex quantitative protein sample analysis by detection of protein-protein interactions using nanopores and cleavable tags. (A) The analyte consists of a protein conjugated with a reporter tag via a cleavable linker (e.g., an antigen, antibody, protein A, or other molecule). (B) Detection of tagged proteins using α-hemolysin nanopores. (1) A mixture of two protein samples labeled with distinct tags is added to the nanopore-containing chip; (2) The analyte protein is captured on the cis side in the vicinity of the α-hemolysin nanopore via protein-protein interactions with a bound primary antibody, receptor, etc. (3) After protein binding and washing, the tags are cleaved off the proteins according to the nature of the cleavable linker; the cleaved tags are electrophoretically driven through the pore to produce unique current blockade signals which are analyzed to quantitatively and qualitatively analyze protein presence.

This invention provides a method for detecting the presence of a plurality of predetermined compounds in a sample which comprises:
(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore;

(d) treating the detectably tagged predetermined compounds bound to said at least one nanopore so as to separate the tag moieties from the predetermined compounds; and (e) detecting said at least one detectable component of each of the tag moieties so released as the tag moieties pass through said at least one nanopore so as to thereby detecting the presence of the plurality of predetermined compounds in the sample.

This invention also provides a method for detecting the presence of a plurality of predetermined compounds in a sample which comprises:

(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore, and wherein each of the tag moieties of said bound detectably tagged predetermined compounds localizes within said at least one nanopore;

(d) detecting said at least one detectable component of each of the tag moieties with said at least one nanopore so as to thereby detecting the presence of the plurality of predetermined compounds in the sample.

This invention further provides a method for determining the quantity of each of a plurality of predetermined compounds in a sample which comprises:

(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore;

(d) treating the detectably tagged predetermined compounds bound to said at least one nanopore so as to separate the tag moieties from the predetermined compounds;

(e) determining the amount of said at least one detectable component of each of the tag moieties so released as the tag moieties pass through said at least one nanopore; and (f) determining, from the amounts of said detectable components determined in step (e), the quantity of each of the plurality of predetermined compounds present in the sample.

This invention even further provides a method for determining the quantity of each of a plurality of predetermined compounds in a sample which comprises:

(a) contacting the sample with a plurality of detectable tag moieties, wherein each detectable tag moiety comprises at least one detectable component, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample;

(b) treating the sample from step (a) to form an electrolyte solution containing the detectably tagged predetermined compounds;

(c) contacting the electrolyte solution from step (b) with at least one nanopore, wherein said at least one nanopore comprises a means for binding each of the detectably tagged predetermined compounds present in the electrolyte solution, under conditions such that the detectably tagged predetermined compounds bind to said at least one nanopore, and wherein each of the tag moieties of said bound detectably tagged predetermined compounds localizes within said at least one nanopore;

(d) determining the amount of said at least one detectable component of each of the tag moieties with said at least one nanopore; and (e) determining, from the amounts of said detectable components determined in step (d), the quantity of each of the plurality of predetermined compounds present in the sample.

In an embodiment of the invention, the methods further comprising a washing step to remove any detectably tagged predetermined compound which is not bound to said at least one nanopore prior to step (d).

In an embodiment of the invention, the predetermined compound is a protein. In a preferred embodiment, the predetermined compound is an antibody. In another embodiment of the invention, the predetermined compound is non-proteinaceous.

In an embodiment of the invention, the tag moiety comprises more than one detectable component. It is contemplated that each such detectable component is independently detectable.

In a further embodiment of the invention, the detectable component is selected from the group consisting of ethylene glycol, an amino acid, a carbohydrate, a peptide, a dye, a fluorescent compound, a chemilluminiscent compound, a mononucleotide, a dinucleotide, a trinucleotide, a tetranucleotide, a pentanucleotide, a hexanucleotide, a polynucleotide, a nucleotide monophopshate, a nucleotide diphosphate, a nucleotide polyphosphate, an aliphatic acid, an aromatic acid, an unsubstituted alcohol or thiol, an alcohol or a thiol substituted with one or more halogens, a cyano group, a nitro group, an alkyl group, an alkenyl group, an alkynyl group, and an azido group.

In certain embodiments, the detectable component of said tag moieties comprises a multiplicity of ethylene glycol units. In a further embodiment, the multiplicity of ethylene glycol units comprises 16, 20, 24, or 36 ethylene glycol units.

In an embodiment of the invention disclosed herein, the tag moiety attaches to the predetermined compound via a cleavable linker. In further embodiments of the invention, the cleavable linker is a photocleavable linker or a chemically cleavable linker.

In one embodiment, the photocleavable linker is a 2-nitrobenzyl linker. In another embodiment, the chemically cleavable linker is an azido linker. In an embodiment, UV light is used to cleave the photocleavable linker. Methods for production of cleavably capped and/or cleavably linked molecules are disclosed in U.S. Pat. No. 6,664,079, which is hereby incorporated by reference.

In an embodiment of the claimed method, at least one of the predetermined compounds present in the sample is a protein and at least one of said tag moieties attaches to the carboxy or amino terminus of said protein.

In another embodiment, at least one of the predetermined compounds present in the sample is a protein and at least one of said tag moieties attaches to a lysine, an arginine, or a cysteine residue of said protein.

In a further embodiment of invention, the nanopore is a biological nanopore, a modified biological nanopore, or a synthetic nanopore. In certain embodiments, the nanopore is proteinaceous, in particular an alpha hemolysin (α-hemolysin).

In yet another embodiment, the nanopore is a solid-state nanopore. In a specific embodiment, the nanopore comprises grapheme. It is contemplate that in certain embodiment the nanopore is in a membrane.

In an embodiment of the invention, the nanopore is part of an array of nanopores. In certain embodiments, each nanopore in said array comprises identical means for binding the detectably tagged predetermined compounds. In certain other embodiments, each nanopore in said array comprises different means for binding the detectably tagged predetermined compounds.

In an embodiment, the means for binding the detectably tagged predetermined compounds is a protein, in particular an antibody. In another embodiment, the means for binding the detectably tagged predetermined compounds is non-proteinaceous.

In an embodiment of the methods disclosed herein, a tag moiety is distinguishable from any other tag moiety based on blockade signature of said tag moiety detectable with said at least one nanopore. In certain embodiments, the blockade signature is result of a change in current amplitude or conductance of said at least one nanopore.

In an embodiment, said at least one nanopore further comprising a mean for ejecting said tag moiety from the nanopore.

This invention also provides a method for detecting interaction of at least two predetermined compounds which comprises;

(a) contacting at least a first predetermined compound present in a sample with a detectable tag moiety, wherein the detectable tag moiety comprises at least one detectable component, under conditions permitting the tag moiety to attach to the predetermined compound present in the sample to form a detectably tagged predetermined compound;

(b) treating the sample from step (a) to form an electrolyte solution containing the detectably tagged predetermined compounds;

(c) contacting the electrolyte solution from step (b) with at least one nanopore, wherein at least a second predetermined compound is immobilized on said at least one nanopore, under conditions permitting the binding of the detectably tagged predetermined compound with the second predetermined compound;

(d) treating the detectably tagged predetermined compound bound to said at least one nanopore so as to separate the tag moiety from the predetermined compound; and (e) detecting said at least one detectable component of the tag moiety so released as the tag moiety passes through said at least one nanopore so as to thereby detecting the interaction of the predetermined compounds.

This invention further provides a method for detecting interaction of at least two predetermined compounds which comprises:

(a) contacting at least a first predetermined compound present in a sample with a detectable tag moiety, wherein the detectable tag moiety comprises at least one detectable component, under conditions permitting the tag moiety to attach to the predetermined compound present in the sample to form a detectably tagged predetermined compound;

(b) treating the sample from step (a) to form an electrolyte solution containing the detectably tagged predetermined compound;

(c) contacting the electrolyte solution from step (b) with at least one nanopore, wherein at least a second predetermined compound is immobilized on said at least one nanopore, under conditions permitting the binding of the detectably tagged predetermined compound with the second predetermined compound, and wherein the tag moiety of said detectably tagged predetermined compound bound to the second predetermined compound localizes within said at least one nanopore;

(d) detecting said at least one detectable component of the tag moiety with said at least one nanopore so as to thereby detecting the interaction of the predetermined compounds.

In an embodiment, the method further comprises a washing step to remove any detectably tagged predetermined compound which is not bound to the second predetermined compound prior to step (d).

In an embodiment of the invention, at least one of the predetermined compounds is a protein. In a specific embodiment, the protein is an antibody. In another embodiment of the invention, at least one of the predetermined compounds is non-proteinaceous.

In an embodiment, the tag moiety comprises more than one detectable component. In a specific embodiment, each detectable component is independently detectable.

In an embodiment of the invention, each of said at least one detectable component of said tag moiety is selected from the group consisting of ethylene glycol, an amino acid, a carbohydrate, a peptide, a dye, a fluorescent compound, a chemilluminiscent compound, a mononucleotide, a dinucleotide, a trinucleotide, a tetranucleotide, a pentanucleotide, a hexanucleotide, a polynucleotide, a nucleotide monophopshate, a nucleotide diphosphate, a nucleotide polyphosphate, an aliphatic acid, an aromatic acid, an unsubstituted alcohol or thiol, an alcohol or a thiol substituted with one or more halogens, a cyano group, a nitro group, an alkyl group, an alkenyl group, an alkynyl group, and an azido group.

In an embodiment of the invention, said at least one detectable component of said tag moiety comprises a multiplicity of ethylene glycol units. In certain specific embodiments, said multiplicity of ethylene glycol units comprises 16, 20, 24, or 36 ethylene glycol units.

In an embodiment of the invention, said tag moiety attaches to the predetermined compound via a cleavable linker. The cleavable linker could be a photocleavable linker or a chemically cleavable linker.

In an embodiment, the predetermined compound present in the sample is a protein and said tag moiety attaches to the carboxy or amino terminus of said protein. In another embodiment, the predetermined compound present in the sample is a protein and said tag moiety attaches to a lysine, an arginine, or a cysteine residue of said protein.

In certain embodiment, said at least one nanopore is a biological nanopore, a modified biological nanopore, or a synthetic nanopore. In a specific embodiment, said at least one nanopore is proteinaceous. In a preferred embodiment, said at least one nanopore is an alpha hemolysin (α-hemolysin).

In another embodiment, said at least one nanopore is a solid-state nanopore. In a further embodiment, the solid-state nanopore comprises graphene.

In an embodiment, said at least one nanopore is in a membrane.

In another embodiment, said at least one nanopore is part of an array of nanopores. In some embodiments, each nanopore in said array comprises an identical immobilized second predetermined compound. In other embodiments, each nanopore in said array comprises a different immobilized second predetermined compound.

In an embodiment, the second predetermined compound is a protein. In a specific embodiment, the protein is an antibody.

In another embodiment, the second predetermined compound is non-proteinaceous.

In an embodiment, said tag moiety produces a blockade signature detectable with said at least one nanopore. In certain embodiment, the blockade signature is result of a change in current amplitude of said at least one nanopore. In certain other embodiment, the blockade signature is result of a change in conductance of said at least one nanopore.

In an embodiment, the sample comprises a plurality of predetermined compounds. In such an embodiment, step (a) further comprises contacting the plurality of predetermined compounds present in the sample with a plurality of detectable tag moieties, under conditions permitting the tag moieties to attach to each of the predetermined compounds present in the sample to form detectably tagged predetermined compounds, wherein each tag moiety uniquely attaches to one of the predetermined compounds present in the sample and is distinguishable from any tag moiety attached to any other predetermined compound present in the sample.

In an embodiment, said at least one nanopore comprises a plurality of predetermined compounds capable of binding to the plurality of detectably tagged predetermined compounds present in the sample.

In an embodiment, said at least one nanopore further comprising a means for ejecting said tag moiety from the nanopore. In a specific embodiment, the means for ejecting said tag moiety from the nanopore consisting of a means to adjust electric field of said nanopore.

This invention also provides a detectable tag moiety for use in the methods disclosed herein which comprises a protein reactive group, at least one detectable component, and a linker connecting the protein reactive group and the at least one detectable component.

In an embodiment, the linker is a cleavable linker. The cleavable linker could be a photocleavable linker or a chemically cleavable linker.

This invention further provides a method for detecting the presence of a plurality of predetermined compounds in a plurality of samples, comprising:
(a) contacting each sample with a nanopore-detectable tag moiety, under conditions permitting the tag moiety to attach to the plurality of predetermined compounds present in the sample to form detectably tagged predetermined compounds for that sample, which are distinguishable from any nanopore-detectable tag moiety attached to similar predetermined compounds from any other sample;
(b) mixing the resulting tagged compounds from the plurality of samples from step (a) and treating them in such a way as to form an electrolyte solution containing the set of detectably and distinguishably tagged predetermined compounds;
(c) contacting the electrolyte solution from step (b) with at least one nanopore, wherein said at least one nanopore comprises a means for specific analyte moiety binding to each of the detectably tagged predetermined compounds in the electrolyte solution, under conditions such that the detectably tagged predetermined compounds bind to said at least one nanopore;
(d) treating the detectably tagged predetermined compounds bound to said at least one nanopore so as to separate the tag moieties from the predetermined compounds; and
(e) detecting said at least one detectable component of each of the tag moieties so released as the tag moieties pass through said at least one nanopore so as to thereby detect the presence of the plurality of predetermined compounds in the plurality of samples.

Each method and process described herein can be performed using compound with cleavable or noncleavable tags.

For the foregoing embodiments, each embodiment disclosed herein is contemplated as being applicable to each of the other disclosed embodiments.

As used herein, and unless stated otherwise, each of the following terms shall have the definition set forth below.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Antibody fragments include, without limitation, Fab fragments, Fv fragments and other antigen-binding fragments.

"Nanopore" includes, for example, a structure comprising (a) a first and a second compartment separated by a physical barrier, which barrier has at least one pore with a diameter, for example, of from about 1 to 10 nm, and (b) a means for applying an electric field across the barrier so that a charged molecule such as DNA, nucleotide, nucleotide analogue, or tag, can pass from the first compartment through the pore to the second compartment. The nanopore ideally further comprises a means for measuring the electronic signature of a molecule passing through its barrier. The nanopore barrier may be synthetic or naturally occurring in part. Barriers can include, for example, lipid bilayers having therein α-hemolysin, oligomeric protein channels such as porins, and synthetic peptides and the like. Barriers can also include inorganic plates having one or more holes of a suitable size. Herein "nanopore", "nanopore barrier" and the "pore" in the nanopore barrier are sometimes used equivalently. It is understood that the electric field of a nanopore may be adjustable. It is also understood that a charged molecule such as DNA, nucleotide, nucleotide analogue, or tag, does not need to pass from the first compartment through the pore to the second compartment in order to produce an electronic signature. Such electronic signature may be produced by localization of the molecule within the pore.

Nanopore devices are known in the art and nanopores and methods employing them are disclosed in U.S. Pat. Nos. 7,005,264 B2; 7,846,738; 6,617,113; 6,746,594; 6,673,615; 6,627,067; 6,464,842; 6,362,002; 6,267,872; 6,015,714; 5,795,782; and U.S. Publication Nos. 2004/0121525, 2003/0104428, and 2003/0104428, each of which are hereby incorporated by reference in their entirety.

"Blockade signature" of a molecule passing through a pore via application of an electronic field shall include, for example, the duration of the nucleotide's passage through the pore together with the observed amplitude of current during that passage. Blockade signature for a molecule is envisioned and can be, for example, a plot of current (e.g. pA) versus time for the molecule to pass through the pore via application of an electric field. Alternatively, blockade signature is also determinable for a molecule which does not pass through a pore. Blockade signature of such a molecule is also envisioned and can be for example, a plot of current (e.g. pA) versus time for the molecule to enter into or pass adjacent to the pore. Herein "blockade signature", "blockade signal", and "electronic signature" are sometime used equivalently.

A specific event diagram is constructed which is the plot of translocation time versus blockade current. This specific event diagram (also referred to as an blockade signature) is used to distinguish molecules by single-channel recording techniques based on characteristic parameters such as translocation current, translocation duration, and their corresponding dispersions in the diagram.

As used herein, a "tag" or a "tag moiety" is any chemical group or molecule that is capable of producing a unique blockade signature detectable with a nanopore. In some cases, a tag comprises one or more of ethylene glycol, an amino acid, a carbohydrate, a peptide, a dye, a fluorescent compound, a chemilluminiscent compound, a mononucleotide, a dinucleotide, a trinucleotide, a tetranucleotide, a pentanucleotide, a hexanucleotide, a polynucleotide, a nucleotide monophopshate, a nucleotide diphosphate, a nucleotide polyphosphate, an aliphatic acid, an aromatic acid, an unsubstituted alcohol or thiol, an alcohol or a thiol substituted with one or more halogens, a cyano group, a nitro group, an alkyl group, an alkenyl group, an alkynyl group, an azido group, or a combination thereof.

As used herein, unless otherwise specified, a tag moiety which is different or distinguishable from the tag moiety of a referenced molecule means that the tag moiety has a different chemical structure from the chemical structure of the other/referenced tag moiety. A tag moiety is different or distinguishable from the tag moiety of a referenced molecule could also mean that the tag moiety has a different blockade signature from the blockade signature of the other/referenced tag moiety.

As used herein, a tag which "localizes" within a pore is a tag located inside or adjacent to the pore. A tag which localizes within a pore does not necessarily pass through or translocate the pore.

As used herein, "proteinaceous" compound means any biopolymer formed from amino acids, such as peptides, proteins, antibodies, antigens, or a fragment or portion thereof. Such compound may be naturally occurring or non-naturally occurring.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n–1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS AND DISCUSSIONS

Building on the success of recent work on developing nanopore-based DNA sequencing, a multiplex digital protein detection and quantification technique using proteins tagged with cleavable PEG molecules of different lengths and nanopore detection is developed. In this approach, a specific antibody is covalently attached in the vicinity of a nanopore. Protein analytes from different samples are labeled with cleavable tags that each produces a distinct current blockade signal in the α-hemolysin nanopore. After capture of the tagged protein samples by the antibodies, the tags are cleaved off the proteins, and identified at the single molecule level as they traverse the nanopore.

I. Design and Synthesize of Cleavable Protein-Labeling Tags

A set of modified poly(ethylene glycol) (PEG) tags has been previously developed for single-molecule sequencing and demonstrated to generate unique current blockade signatures when traversing a nanopore. Synthetic derivatives of these tags are developed, which are capable of efficiently conjugating with protein analytes or antibodies via photocleavable or chemically cleavable linkers to allow their subsequent identification in the nanopore.

Figure 2:
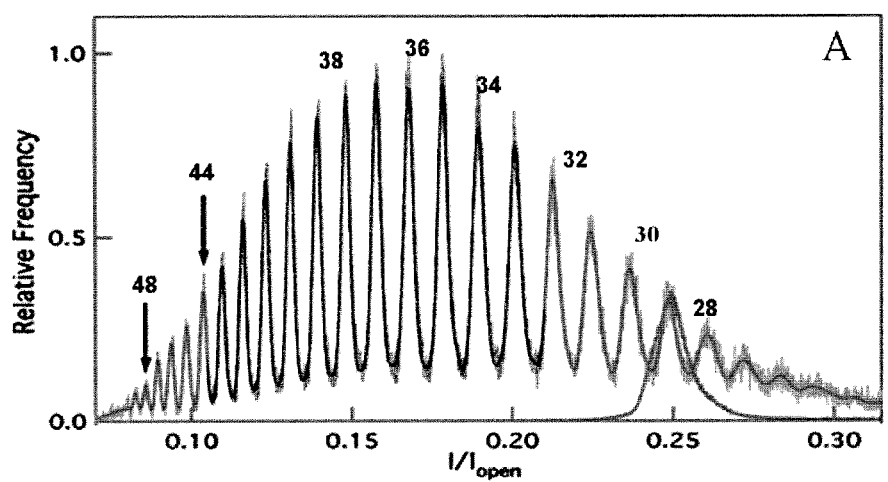
FIG. 2. Correlation between conductance signatures and mass distribution of a polydisperse mixture of PEG oligomers (red) during their transit through a single nanopore as compared with a 29-ethylene glycol unit PEG polymer (blue). The conductance based mass spectrum clearly resolves the repeat units of PEG within the 30-50 monomer unit range [Robertson et al. 2007].

Design of the cleavable tag structure is shown in FIG. 1A and consists of three distinct components: a protein reactive group, a cleavable linker and a nanopore tag. A This design is based on studies of the transit of PEG molecules of different molecular size through the α-hemolysin nanopore [Robertson et al. 2007] and experience in designing cleavable linkers for DNA sequencing by synthesis with reversible terminators bearing fluorescent tags [Guo et al. 2008 and Seo at al. 2005]. Robertson et al. demonstrated that the transit of polydisperse PEG molecules through a *Staphylococcus aureus* α-hemolysin nanopore causes distinct current blockade states that generate characteristic conductance signatures at single-molecule level (FIG. 2), which correlate with the molecular weight of individual PEG molecules. In addition to conductance reduction, the residence time within the nanopore increases linearly with PEG molecular weight [Robertson et al. 2007]. Both of these characteristics can be employed to design recognizable tags for protein labeling as demonstrated below.

A scheme of the method for detection of tagged proteins using α-hemolysin nanopores is shown in FIG. 1B. In this scheme, a mixture of two protein samples labeled with distinct tags is added to the nanopore-containing chip; the analyte protein is captured on the cis side in the vicinity of the α-hemolysin nanopore via protein-protein interactions with a bound primary antibody or receptor; after protein binding and washing, the tags are cleaved off the proteins according to the nature of the cleavable linker; the cleaved tags are electrophoretically driven through the pore to produce unique current blockade signals which are analyzed to quantitatively and qualitatively determine protein presence. A given tag traversing the nanopore causes a current blockade signature of characteristic amplitude and duration, resulting in tag recognition and quantification. As each blockade event occurs within a millisecond, tens of thousands of tags can be analyzed in a short time, their counts providing a digital measure of the analytes' relative abundance in the samples at the single molecule level.

There are a number of chemical transformations which can be used for protein conjugation with the nanopore tags. Beside the C- or N-terminus of proteins, other modification sites include lysines and arginines, which can be modified by treatment with NHS esters or isothiocyanates, and cysteine thiols modified with maleimides or α-halo-carbonyl compounds.

In this instance, the amino group on lysines or the thiol group of cysteines is modified with a cleavable linker-attached PEG molecule. Since most proteins have several lysines, but relatively few unreacted cysteines, conditions can be optimized for a range of label densities. The linker can be either a chemically or photochemically cleavable linker that would react with the lysines or cysteines on proteins and release PEG molecules after cleavage with tris(2-carboxyethyl)phosphine (TCEP) or with light at 350 nm, respectively; released PEG molecules are identified by the current blockade signal on the nanopore.

a) Chemically Cleavable Linkers

Figure 3:
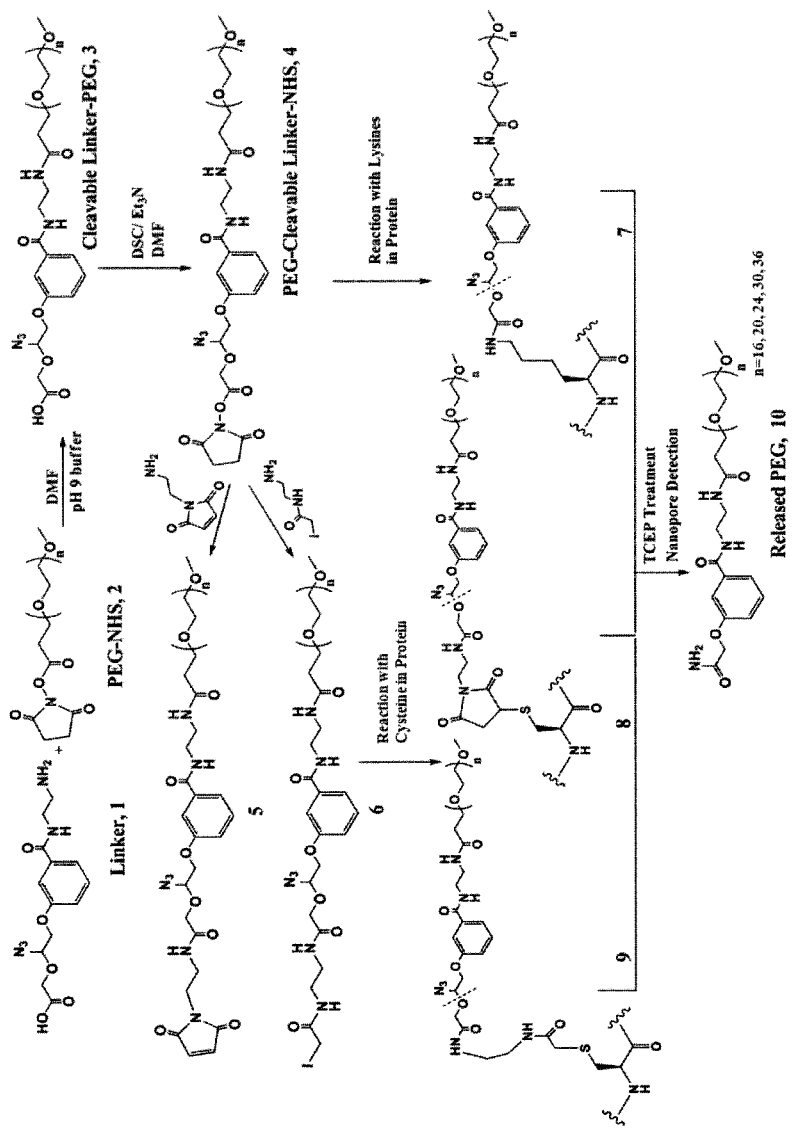
FIG. 3. Synthesis of chemically cleavable linkers for protein labeling. Dotted lines indicate the cleavage site on treatment with TCEP.

An example of synthesis of a chemically cleavable linker is shown in FIG. 3. The azido-linker (1) [Guo et al. 2008] is reacted with an appropriate size PEG-NHS ester (2) to provide an azido-cleavable linker-PEG molecule (3). The acid group in (3) is activated with DSC/DMF to provide the PEG-cleavable linker-NHS ester (4) which is reacted with the lysine amino group in the protein to provide a labeled protein similar to (7).

Alternatively, compound (4) can be derivatized with functional groups (maleimides or iodoacetamides) which react efficiently with the thiol group on cysteine. Thus compound (4), on reaction with amino-maleimide or iodoacetamide-ethylamine, yields compounds (5) and (6), respectively. These compounds, upon reaction with the cysteine thiol group, provide labeled proteins similar in structure to (8) and (9), respectively. Upon treatment with TCEP, the azido linked PEG-protein molecules cleave to release PEG molecules of structure (10), which pass through the nanopore and produce the resulting current blockade signal.

b) Photochemically Cleavable Linkers

Figure 4:
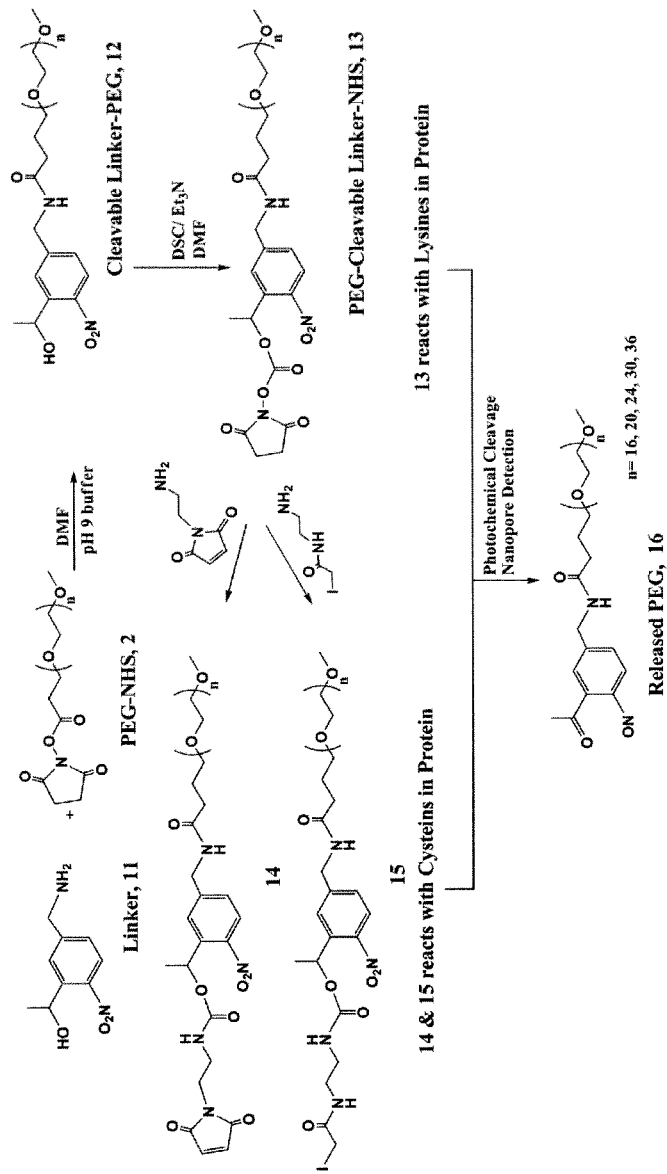
FIG. 4. Synthesis of a photochemically cleavable linker for protein labeling using a nitrobenzyl based linker as the starting material. Dotted lines indicate the cleavage site on treatment with TCEP.

Photochemically cleavable linkers are synthesized using similar methodology as the synthesis of chemically cleavable linkers, except that a nitrobenzyl based linker (11) [Seo et al. 2005] is used as the starting material, as shown in FIG. 4. Remainder of the synthesis scheme is similar to that of chemically cleavable linkers, and provides photochemically cleavable linkers (13)-(15). These linkers, after labeling lysines or cysteines on proteins and photochemical cleavage, provide PEG-linkers similar to structure (16).

II. Test Tags for Coupling, Cleavage, and Nanopore Discrimination

Attaching the tags to either streptavidin or to the Fc portion of a rabbit IgG antibody allows use of biotin or anti-rabbit antibodies as capture agents in later analyses. Gel shift assays are used to confirm attachment and cleavage of the tags. Different molecular tags synthesized are evaluated for ability to quantitatively attach to protein samples and allow subsequent cleavage at high efficiency in order to capture signatures in the nanopore. Based on the results of these experiments, the best tag-linker configurations are selected for labeling and detection, or redesigned to improve their performance, if necessary.

In particular, PEG tags of various lengths coupled with protein-reactive groups via different cleavable linkers are tested for performance efficiency in coupling and cleavage, as well as for discrimination of their current blockade signals in a nanopore. The goal of these experiments is to select the optimal tags with coupling and cleavage chemistries effective for the analyte proteins and chemically compatible with the nanopore environment and electronic detection.

To test protein-protein interactions, tag cleavage, and nanopore detection, commercially available streptavidin (Life Technologies) and polyclonal rabbit IgG (Thermo Fisher Scientific) are used as the protein analytes. Exclusion of any particular antigen from these studies simplifies the analysis. By using highly standardized reactions with primary and secondary antibody interactions instead, the conditions found here can be immediately adapted for full antigen-antibody sandwich methods.

Figure 5:
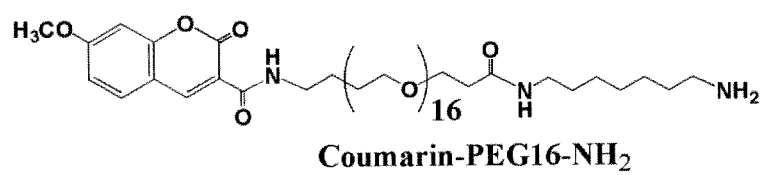
FIG. 5. Monodisperse coumarin-PEG derivatives of different size.
Figure 5:
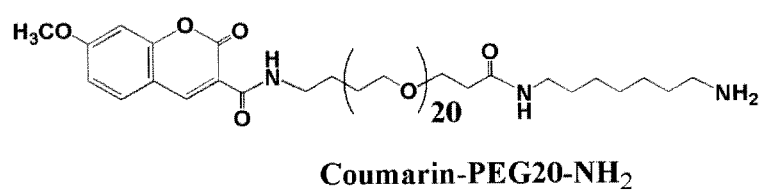
Figure 5:
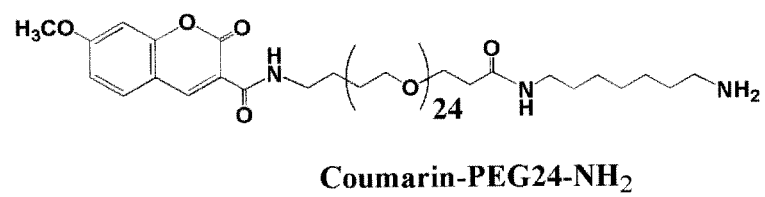
Figure 5:
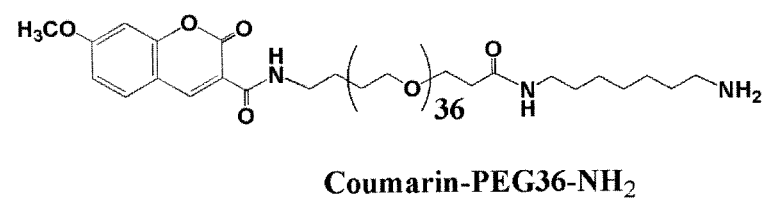

PEG tags are attached to the amino group on lysine of the analyte proteins using standard NHS chemistry, and the optimal conjugation conditions are determined using protein gel shift assays. The protein labeling extent is found using PEG tags derivatized with coumarin to allow spectrophotometric detection at 350 nm where protein absorption of light is low. Several coumarin-PEG derivative compounds have been successfully synthesized for nanopore blockade evaluation (FIG. 5).

Cleavage reaction conditions are determined in a similar way. Tag-labeled proteins (streptavidin or rabbit IgG) are treated with TCEP or, in the case of photocleavable tags, irradiated with near-UV light ($\lambda$-365 nm). Cleavage is evaluated for completion by protein gel shift and spectroscopic measurements.

To evaluate the discrimination of the cleaved tags with the nanopore the tagged proteins are captured on a solid phase biotin-coated 96-well plates (Thermo Fisher Scientific) for PEG-tagged streptavidin; and on a solid phase goat-anti-rabbit polyclonal antibody-coated 96-well plates (Thermo Fisher Scientific) for PEG-tagged rabbit IgG. Follow by inducing release of the tags and counting of the released tags in bulk at single molecule level using a solitary $\alpha$-hemolysin nanopore patch clamp electrode assembly by dipping the patch clamp directly into the wells of the plate.

Figure 6:
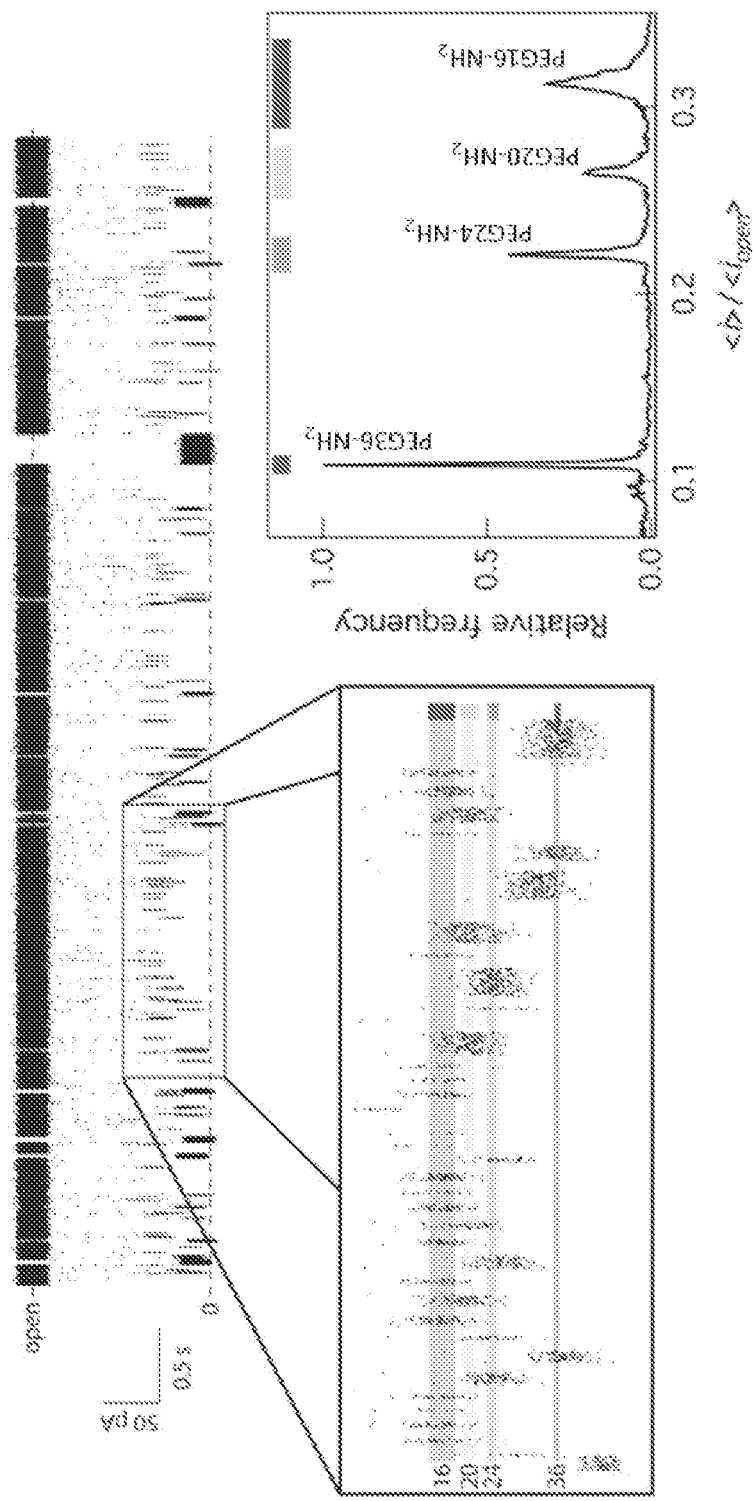
FIG. 6. Discrimination of a mixture of coumarin-PEG tags of different sizes in a α-hemolysin nanopore at single molecule level. Left: time series data indicates that when PEG tags enter a single α-hemolysin channel, they cause current blockades that are characteristic in their duration and amplitude. Right: frequency histogram of the mean current blockade caused by individual molecules and expressed as ratio of current blocked vs open channel, which shows baseline resolution with a 10 kHz measurement bandwidth. The colored bars at the top represent the 6 σ distribution of the data, which suggests that a single tag could be discriminated with accuracy better than 1 in 300,000 events [Kumar et al. 2012].

Discrimination for four coumarin-PEG derivatives of the sizes of 16, 20, 24, and 36 monomer units is shown in FIG. 6, an 8-second current trace produced by a mixture of these PEG oligomers transiting the solitary nanopore. A time series data shown on left side indicates that when PEG tags enter a single $\alpha$-hemolysin channel, they cause current blockades that are characteristic in their duration and amplitude. On right side, a frequency histogram of the mean current blockade caused by individual molecules and expressed as ratio of current blocked vs open channel shows baseline resolution with a 10 kHz measurement bandwidth. The colored bars at the top represent the 6 $\sigma$ distribution of the data, which suggests that a single tag could be discriminated with accuracy better than 1 in 300,000 events.

As the analysis of the blockage signals illustrates, data show excellent discrimination of the selected PEG tags over a 6 $\sigma$ confidence interval and also demonstrate the speed and accuracy of the quantitative analysis the released tags. In particular, there is a substantial gap between PEG sizes of 24 and 36 ethylene glycol units. Based on this result, one could select different length PEGs (available commercially from Quanta Biodesign Ltd. or other suppliers) and monitor their nanopore blockade signals for additional tags within this molecular size range that retain a similar level of discrimination.

Noteworthy as well is the remarkably low expected noise originating from the transit of non-tag molecules through the nanopore due to the high selectivity of the nanopore aperture. Majority of the polymers, including proteins, are incapable of entering the pore, and the smaller molecules produce barely detectable blockage of the pore. Thus, rational chemical design of cleavable linkers and selection of appropriate PEG polymers generate a series of optimal tags suitable for discrimination of multiplex samples using nanopore.

III. Multiplex Quantification of Protein Samples Labeled with Different Tags Using Nanopores A library of PEG tags that yield distinct nanopore signals is used to test the multiplex quantification scheme by capturing protein samples labeled with different tags using ligands or antibodies. Sensitivity and dynamic range of the nanopore detection method is also determined and compared with fluorescent and colorimetric detection.

Sample multiplexing can also be accomplished by binding such a library of tags that yield distinct nanopore signals to the same protein derived from different samples, different individuals, or different samples or individuals before, during and following some change, treatment or perturbation. Again, as for protein multiplexing, sensitivity and dynamic range can be determined and compared with fluorescent and colorimetric methods.

The experiments involve selecting a series of well discriminated tags, attaching the tags to streptavidin (SA) or rabbit antibodies, mixing the tagged proteins in different ratios, and preparing serial dilutions of the mixtures. The nanopore tags are also mixed with SA-alkaline phosphatase (Thermo Fisher Scientific), SA-AlexaFluor 488 (Life Technologies) or, in the case of the antibody reaction, with similarly labeled rabbit IgG antibodies (available from Thermo Fischer Scientific).

Biotin or anti-rabbit IgG antibodies are attached to the wells of 96-well plates to perform the binding and collection of the cleaved tags for detection in the nanopore. After performing the analyte capture using appropriately coated 96-well plates and induce the tag cleavage, tag quantification is performed using the patch clamp technique with a single nanopore and quantitation is performed in the same wells using fluorescent or colorimetric detection.

Comparing the tag counts on the trans side of the nanopore with the predefined proportions on the cis side allows evaluation of the concentration estimation using the nanopore, estimate the dynamic and quantitative (free of Poisson noise) range of the method in the presence of different tags, and directly compare them with the sensitivity and the performance of other non-nanopore based methods, which also serve as internal controls for analyte capture.

Mixtures of proteins with different tags are detected in the expected ratios. Differences in tag-labeling efficiencies associated with variations in amino acid compositions among different antigens do not present an obstacle for the quantification because differences in the number of tags coupled with each antigen type can be inferred from their amino acid sequence, verified experimentally, and corrected in downstream analysis.

IV. Detection of Molecular Interactions

Figure 7:
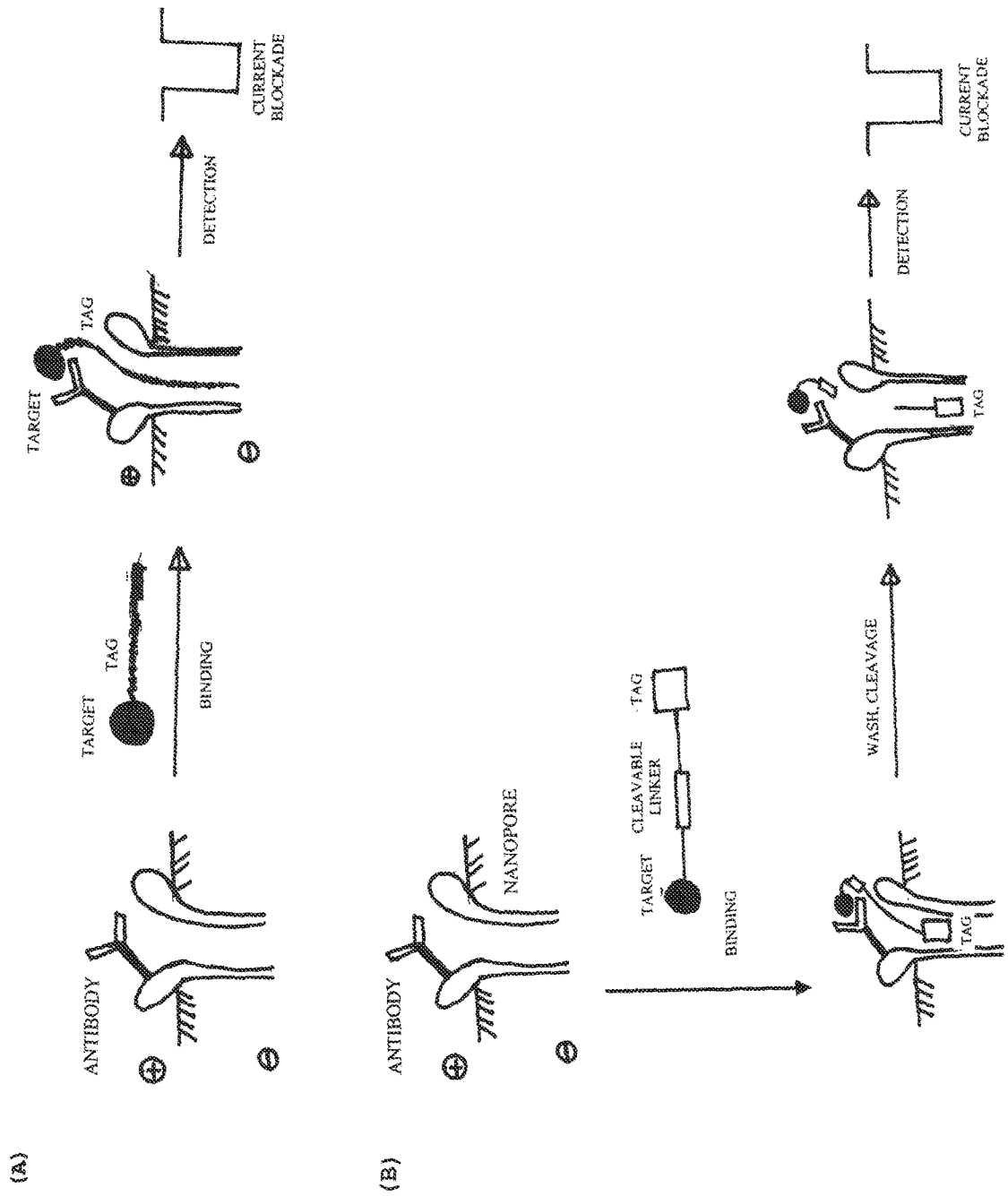
FIG. 7. Detection of interactions (an antibody and antigen interaction is used as an example) of tagged compounds using nanopores. (A) An analyte consists of a target protein conjugated with a reporter tag (e.g., an antigen, antibody, protein A, or other molecule). The tagged analyte binds to an antibody immobilized on top of the nanopore, the tag which has been designed to have a positive charge will enter the nanopore, causing a unique electrical current blockade, which can be used to identify the target molecule. (B) An analyte consists of a target protein conjugated with a reporter tag (e.g., an antigen, antibody, protein A, or other molecule) through a cleavable linker. The tagged analyte binds to an antibody immobilized on top of the nanopore, upon cleavage of the linker, the tag which has been designed to have a positive charge will pass through the nanopore, causing a unique electrical current blockade, which can be used to identify the target molecules.

FIG. 7 illustrates detection of molecular interactions, using an antibody and antigen interaction as an example, with nanopores and tags. As shown in FIG. 7(A), an analyte consists of a target protein conjugated with a reporter tag (e.g., an antigen, antibody, protein A, or other molecule). When the tagged analyte binds to the antibody immobilized on the top of the nanopore, the tag which has been designed to have a positive charge will enter the nanopore, causing a unique electrical current blockade, which can be used to identify the target molecules. As shown in FIG. 7(B), an analyte also could consist of a target protein conjugated with a reporter tag (e.g., an antigen, antibody, protein A, or other molecule) through a cleavable linker. When the tagged analyte binds to the antibody immobilized on the top of the nanopore, upon cleavage of the linker, the tag which has been designed to have a positive charge will pass through the nanopore, causing a unique electrical current blockade, which can be used to identify the target molecules.

DISCUSSION

The explosive development of massively parallel nucleic acid sequencing and quantification methodology and associated cost reductions during the last decade have revolutionized mutation and polymorphism detection, transcriptional regulation of gene expression, and numerous other genome scale studies. Indeed, the high-throughput nature of these technologies has created entire new disciplines in functional genomics and systems biology. However, analysis of gene regulation at the level of protein synthesis, like proteomics in general, lags behind nucleic acid analysis in its throughput, sensitivity and automation. Among the major complications in developing high throughput proteomics are relatively poor stability of proteins as analytes, high heterogeneity of protein analytes, and the requirement for a much wider dynamic range of detection with increased demand for sensitivity approaching the single molecule detection level. This need is not easily met by existing technologies which use fluorescent or colorimetric measurements.

Building on the success of recent work on developing nanopore-based DNA sequencing, a technique for multiplex digital protein detection and quantification using PEG-tagged proteins and nanopore array detection is developed. In an example of this approach, a specific antibody is covalently attached in the vicinity of a nanopore. Analyte proteins from different samples are labeled with cleavable tags that produce a distinct current blockade signal in the α-hemolysin nanopore. After capture of the tagged protein samples by the antibodies, the tags are cleaved off the proteins and identified at the single molecule level electronically as they traverse the nanopore. The advantage of this approach is generation of a digital output for the protein quantification with single molecule detection capability; by setting arbitrary upper detection limits, the technique permits characterization of either a wide range of protein concentrations or discrimination of very small changes in protein levels. Thus, the technique has scalability and miniaturization comparable to the most advanced current single molecule genomic methods. The nanopore detection technique based on cleavable molecular tags addresses shortcomings of existing protein arrays approach, which is based on antibody interaction with fluorescently labeled antigens or secondary antibodies. While there are currently several applications of nanopore-based analytics, application of nanopore for quantification of protein-protein interactions with multiplex tags is novel.

These experiments elucidate major parameters for this protein detection method, estimate the method's sensitivity, and define operational conditions utilizing a library of cleavable molecular tags and a single α-hemolysin nanopore. The detection system use a streptavidin-biotin system and a sandwich antibody detection scheme in which the primary antibody is attached to a surface and the cleavable poly(ethylene glycol) (PEG) tag is attached to the antigen (or to a secondary antibody for more efficient multi-nanopore arrays). Result obtained with this method is compared with result of ELISAs with fluorescent and colorimetric detection.

Developed based on existing method using nanopores and cleavable tags for DNA sequencing, this protein detection method consists of (1) labeling protein analytes, antigens or secondary antibodies with photocleavable or chemically cleavable tags; (2) reacting the resulting molecules with nanopore arrays in which antibodies specific to each protein analyte are associated with specific individual nanopores; and (3) after binding and washing, cleaving the tags and identifying them during their traversal of the adjacent nanopore. Different tags producing distinct current blockade signatures define the sample source, while registering the number of blockade events quantifies the number of tags of each type transiting the nanopore. All other assay components either do not enter the nanopores and/or are washed away between assay steps.

The three steps outlined above: cleavable tag design, capture of tagged protein samples, and detection using electronic identification of cleaved tags at single molecule resolution with a nanopore, bring the analysis to the nanoscale while at the same time permitting scale-up of the overall throughput for simplified whole-proteome quantitation.

This protein detection method has significant advantages over current fluorescent antibody-based proteomics arrays and may form a basis for creating protein detection sensors with the advantages of traditional semiconductor technologies using nanopore-based sensor arrays using inexpensive and highly scalable standardized semiconductor technologies being developed.

Additionally, regardless of the type of tag, an important aspect of this method involves labeling different compounds with tags having distinguishable current blockade signatures generated as result of the tags traverse the nanopore. This differs substantially from existing protein detection system in which an aptamer binds to a protein to form a complex in solution on the cis side of a nanopore, where the complex are attracted to the nanopore by the aptamer, and generates a two-step blockade current, first due to the aptamer entering the pore and the second due to the protein which blocks but does not enter the pore and is subsequently cleaved to allow the next aptamer to enter. The existing process requires measuring, and account for, current blockade signatures for unbound aptamer and aptamer-free protein in any quantitative measurement schemes.

This approach generates a digital output for the protein quantification with near-single molecule per cell detection capability. By setting arbitrary upper detection limits, the technique permits characterization of a wide range of protein concentrations or discrimination of very small changes in protein abundance. The technique has scalability and miniaturization comparable to the most advanced current single molecule genomic methods (e.g., direct RNA-Seq). Eventually, the approach can be adopted to use nanopore arrays capable of characterizing hundreds to thousands of proteins at once from multiple tissues at the single-molecule level rapidly and at low cost, and follow changes in these proteins during different pathological states.

These experiments establish the method and exploring its range of performance. Once established, the method can be applied as a detection method of choice with existing protein microarrays and for other proteomics methods where demands for single molecule detection and a simplified electronic readout are high. Potential obstacles inherent to proteomics beyond detection, such as differences in labeling extent and variable affinities, can be overcome using more reliable and uniform binding counterparts such as aptamers or affibodies, build experimentally based correction methods for differences in labeling, design secondary detection methods, and more elaborate sandwich schemes to enhance sensitivity. This method has advantages over fluorescent and colorimetric detection in that it uses standard semiconductor arrays with digital rather than analog detection output permitting counting of events at the single molecule level. It has virtually unrestricted dynamic range, low cost, and high scalability from detection of a handful of specific proteins to whole proteome analysis. This method is also capable of complementing, at the level of proteomics, the advances in high throughput DNA and RNA techniques in such diverse areas of analysis as translational regulation of gene expression, immune response biomarker identification, protein-protein interaction profiling, translational regulation by miRNAs, and non-PCR methods for detection of pathogens.

REFERENCES

Angenendt P., "Progress in protein and antibody microarray technology", Drug Discov. Today 2005; 10(7):503-511.

Burnette W N. "'Western blotting': electrophoretic transfer of proteins from sodium dodecyl sulfate-polyacrylamide gels to unmodified nitrocellulose and radiographic detection with antibody and radioiodinated protein A", Anal. Biochem. 1981; 112(2):195-203.

Bussow K, Cahill D, Nietfeld W, Bancroft D, Scherzinger E, Lehrach H, Walter G. "A method for global protein expression and antibody screening on high-density filters of an arrayed cDNA library", Nucleic Acids Res, 1998; 26(21):5007-5008.

Cahill D J. "Protein and antibody arrays and their medical applications", J. Immunol. Methods, 2001; 250(1-2):81-91.

de Wildt R M, Mundy C R, Gorick B D, Tomlinson I M. "Antibody arrays for high-throughput screening of antibody-antigen interactions", Nat. Biotechnol, 2000; 18(9):989-994.

Engvall E, Perlmann P. "Enzyme-linked immunosorbent assay (ELISA), Quantitative assay of immunoglobulin", G. Immunochemistry 1971; 8(9):871-874.

Gygi S P, Rist B, Gerber S A, Turecek F, Gelb M H, Aebersold R. "Quantitative analysis of complex protein mixtures using isotope-coded affinity tags", Nat. Biotechnol. 1999; 17(10):994-999.

Guerrera I C, Kleiner O. "Application of mass spectrometry in proteomics", Biosci. Rep. 2005; 25(1-2):71-93.

Guo J, Xu N, Li Z, Zhang S, Wu J, Kim D H, Sano Marma M, Meng Q, Cao H, Li X, Shi S, Yu L, Kalachikov S, Russo J J, Turro N J, Ju J. "Four-color DNA sequencing with 3'-O-modified nucleotide reversible terminators and chemically cleavable fluorescent dideoxynucleotides", Proc. Natl. Acad. Sci. USA 2008; 105(27):9145-9150

Klose J. "Protein mapping by combined isoelectric focusing and electrophoresis of mouse tissues: a novel approach to testing for induced point mutations in mammals", Humangenetik 1975; 26(3):231-243.

Kumar S. Tao C, Chien M, Hellner B, Balijepalli A, Robertson J W, Li Z, Russo J J, Reiner J E, Kasianowicz J J, Ju J. "PEG-labeled nucleotides and nanopore detection for single molecule DNA sequencing by synthesis", Sci. Rep. 2012; 2:684.

O'Farrell P H. "High resolution two-dimensional electrophoresis of proteins", J. Biol. Chem. 1975; 250(10):4007-4021.

Robertson J W, Rodrigues C G, Stanford V M, Rubinson K A, Krasilnikov O V, Kasianowicz J J. "Single-molecule mass spectrometry in solution using a solitary nanopore", Proc. Natl. Acad. Sci. USA 2007; 104(20):8207-8211.

Seo T S, Bai X, Kim D H, Meng Q, Shi S, Ruparel H, Li Z, Turro N J, Ju J. "Four-color DNA sequencing by synthesis on a chip using photocleavable fluorescent nucleotides", Proc. Natl. Acad. Sci. USA 2005; 102(17):5926-5931.

Yalow R S, Berson S A. "Immunoassay of endogenous plasma insulin in man", J. Clin. Invest. 1960; 39:1157-1175.

What is claimed is:

1. A method for detecting interaction of at least two predetermined compounds which comprises:
    (a) contacting at least a first predetermined compound present in a sample with a detectable tag moiety, wherein the detectable tag moiety comprises at least one detectable component, under conditions permitting the tag moiety to be conjugated to the predetermined compound present in the sample to form a detectably tagged predetermined compound;
    (b) treating the sample from step (a) to form an electrolyte solution containing the detectably tagged predetermined compounds;
    (c) contacting the electrolyte solution from step (b) with at least one nanopore, wherein at least a second predetermined compound is immobilized on the top of said at least one nanopore, under conditions permitting the binding of the detectably tagged predetermined compound with the second predetermined compound;
    (d) treating the detectably tagged predetermined compound bound to said at least one nanopore so as to separate the tag moiety from the predetermined compound; and
    (e) detecting said at least one detectable component of the tag moiety so released as the tag moiety passes through said at least one nanopore so as to thereby detect the interaction of the predetermined compounds.

2. A method for detecting interaction of at least two predetermined compounds which comprises:
    (a) contacting at least a first predetermined compound present in a sample with a detectable tag moiety, wherein the detectable tag moiety comprises at least one detectable component, under conditions permitting the tag moiety to be conjugated to the predetermined compound present in the sample to form a detectably tagged predetermined compound;
(b) treating the sample from step (a) to form an electrolyte solution containing the detectably tagged predetermined compound;
(c) contacting the electrolyte solution from step (b) with at least one nanopore, wherein at least a second predetermined compound is immobilized on the top of said at least one nanopore, under conditions permitting the binding of the detectably tagged predetermined compound with the second predetermined compound, and wherein the tag moiety of said detectably tagged predetermined compound bound to the second predetermined compound localizes within said at least one nanopore;
(d) detecting said at least one detectable component of the tag moiety with said at least one nanopore so as to thereby detect the interaction of the predetermined compounds.

3. A method for detecting the presence and quantity of a plurality of predetermined compounds in a plurality of samples, comprising:
(a) contacting each sample with a nanopore-detectable tag moiety wherein the detectable tad moiety comprises at least one detectable component, under conditions permitting the tag moiety to be conjugated to the plurality of predetermined compounds present in the sample to form detectably tagged predetermined compounds for that sample, which are distinguishable from any nanopore-detectable tag moiety attached to similar predetermined compounds from any other sample;
(b) mixing the resulting tagged compounds from the plurality of samples from step (a) and treating them in such a way as to form an electrolyte solution containing the set of detectably and distinguishably tagged predetermined compounds;
(c) contacting the electrolyte solution from step (b) with at least one nanopore, wherein said at least one nanopore comprises a means on the top of said at least one nanopore for specific analyte moiety binding to each of the detectably tagged predetermined compounds in the electrolyte solution, under conditions such that the detectably tagged predetermined compounds bind to said at least one nanopore, thereby immobilizing the detectably tagged predetermined compounds on the top of the at least one nanopore;
(d) treating the detectably tagged predetermined compounds bound to said at least one nanopore so as to separate the tag moieties from the predetermined compounds; and
(e) detecting said at least one detectable component of each of the tag moieties so released as the tag moieties pass through said at least one nanopore so as to thereby detect the presence of the plurality of predetermined compounds in the plurality of samples
(f) determining the amount of said at least one detectable component of each of the tag moieties so released as the tag moieties pass through said at least one nanopore; and
(g) determining, from the amounts of said detectable components determined in step (e), the quantity of each of the plurality of predetermined compounds present in the sample.

4. The method of claim 3, wherein the plurality of predetermined compounds are proteins.

5. The method of claim 3, wherein each detectable component is independently detectable.

6. The method of claim 3, wherein each of said at least one detectable component of said tag moieties is selected from the group consisting of ethylene glycol, an amino acid, a carbohydrate, a peptide, a dye, a fluorescent compound, a chemiluminescent compound, a mononucleotide, a dinucleotide, a trinucleotide, a tetranucleotide, a pentanucleotide, a hexanucleotide, a polynucleotide, a nucleotide monophopshate, a nucleotide diphosphate, a nucleotide polyphosphate, an aliphatic acid, an aromatic acid, an unsubstituted alcohol or thiol, an alcohol or a thiol substituted with one or more halogens, a cyano group, a nitro group, an alkyl group, an alkenyl group, an alkynyl group, and an azido group.

7. The method of claim 3, wherein said at least one detectable component of said tag moieties comprises a multiplicity of ethylene glycol units.

8. The method of claim 7, wherein said multiplicity of ethylene glycol units comprises 16, 20, 24, or 36 ethylene glycol units.

9. The method of claim 3, wherein at least one of said tag moieties attaches to the predetermined compound via a cleavable linker.

10. The method of claim 9, wherein the cleavable linker is a chemically cleavable linker or a photocleavable linker.

11. The method of claim 3, wherein the predetermined compound present in the sample is a protein and said tag moiety attaches to the carboxy or amino terminus of said protein.

12. The method of claim 3, wherein the predetermined compound present in the sample is a protein and said tag moiety attaches to a lysine, an arginine, or a cysteine of said protein.

13. The method of claim 3, wherein said at least one nanopore is a biological nanopore, a modified biological nanopore, or a synthetic nanopore.

14. The method of claim 3, wherein said at least one nanopore is an alpha hemolysin (α-hemolysin).

15. The method of claim 3, wherein said at least one nanopore is a solid-state nanopore.

16. The method of claim 15, wherein the solid-state nanopore comprises graphene.

17. The method of claim 3, wherein said at least one nanopore is in a membrane.

18. The method one of claim 3, wherein said at least one nanopore is part of an array of nanopores.

19. The method of claim 18, wherein each nanopore in said array comprises identical means for binding the detectably tagged predetermined compounds.

20. The method of claim 18, wherein each nanopore in said array comprises different means for binding the detectably tagged predetermined compounds.

21. The method of claim 3, wherein the means for binding the detectably tagged predetermined compounds is a protein.

22. The method of claim 3, wherein each tag moiety is distinguishable from any other tag moiety based on blockade signature of said tag moiety detectable with said at least one nanopore.

23. The method of claim 22, wherein the blockade signature is result of a change in current amplitude of said at least one nanopore.

24. The method of claim 3, wherein said at least one nanopore further comprises a means for ejecting said tag moiety from the nanopore.

25. The method of claim 3, wherein the detectably tagged predetermined compounds are bound to a protein or antibody.

\* \* \* \* \*